(12) United States Patent
Garnier et al.

(10) Patent No.: US 7,479,578 B2
(45) Date of Patent: Jan. 20, 2009

(54) HIGHLY WETTABLE—HIGHLY FLEXIBLE FLUFF FIBERS AND DISPOSABLE ABSORBENT PRODUCTS MADE OF THOSE

(75) Inventors: Gil Bernard Didier Garnier, Neenah, WI (US); Elizabeth Ann Allison, Troy, OH (US); Mary Alice Berceau, DePere, WI (US); Troy Michael Runge, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 834 days.

(21) Appl. No.: 10/741,035

(22) Filed: Dec. 19, 2003

(65) Prior Publication Data

US 2005/0137547 A1 Jun. 23, 2005

(51) Int. Cl.
*A61F 13/20* (2006.01)
*B32B 13/04* (2006.01)

(52) U.S. Cl. .............. 604/375; 604/369; 604/379; 604/371; 604/372; 604/373; 604/376; 604/377; 604/374; 604/365; 604/368; 428/446; 428/447; 428/448; 428/449

(58) Field of Classification Search .......... 604/367, 604/374, 368, 359, 360, 361, 369–373, 375–377, 604/365; 428/446–449
See application file for complete search history.

(56) References Cited

U.S. PATENT DOCUMENTS

| | | |
|---|---|---|
| 2,757,150 A | 7/1956 | Heritage |
| 3,224,926 A | 12/1965 | Bernardin |
| 3,241,553 A | 3/1966 | Steiger |
| 3,440,135 A | 4/1969 | Chung |
| 3,556,932 A | 1/1971 | Cosica et al. |
| 3,556,933 A | 1/1971 | Williams et al. |
| 3,700,623 A | 10/1972 | Kelm |
| 3,772,076 A | 11/1973 | Keim |
| 3,855,158 A | 12/1974 | Petrovich et al. |
| 3,899,388 A | 8/1975 | Petrovich et al. |
| 4,128,692 A | 12/1978 | Reid |
| 4,129,528 A | 12/1978 | Petrovich et al. |
| 4,147,586 A | 4/1979 | Petrovich et al. |
| 4,222,921 A | 9/1980 | Van Eenam |
| 4,297,860 A | 11/1981 | Pacifici et al. |
| 4,303,471 A | 12/1981 | Laursen |
| 4,357,827 A | 11/1982 | McConnell |
| 4,425,186 A | 1/1984 | May et al. |
| 4,432,833 A | 2/1984 | Breese |
| 4,440,597 A | 4/1984 | Wells et al. |
| 4,469,746 A | 9/1984 | Weisman et al. |
| 4,508,860 A | 4/1985 | Hawes |
| 4,514,345 A | 4/1985 | Johnson et al. |
| 4,528,239 A | 7/1985 | Trokhan |
| 4,529,480 A | 7/1985 | Trokhan |
| 4,556,450 A | 12/1985 | Chuang et al. |
| 4,584,357 A | 4/1986 | Harding |
| 4,600,462 A | 7/1986 | Watt |
| 4,663,220 A | 5/1987 | Wisneski et al. |
| 4,773,110 A | 9/1988 | Hopkins |
| 4,898,642 A | 2/1990 | Moore et al. |
| 4,950,545 A | 8/1990 | Walter et al. |
| 5,057,166 A | 10/1991 | Young, Sr. et al. |
| 5,059,282 A | 10/1991 | Ampulski et al. |
| 5,068,009 A | 11/1991 | Jokinen et al. |
| 5,071,675 A | 12/1991 | Gupta et al. |
| 5,098,522 A | 3/1992 | Smurkoski et al. |
| 5,223,090 A | 6/1993 | Klungness et al. |
| 5,226,992 A | 7/1993 | Morman |
| 5,227,242 A | 7/1993 | Walter et al. |
| 5,230,776 A | 7/1993 | Andersson et al. |
| 5,246,545 A | 9/1993 | Ampulski et al. |
| 5,260,171 A | 11/1993 | Smurkoski et al. |
| 5,275,700 A | 1/1994 | Trokhan |
| 5,300,192 A | 4/1994 | Hansen et al. |
| 5,328,565 A | 7/1994 | Rasch et al. |
| 5,334,289 A | 8/1994 | Trokhan et al. |
| 5,338,352 A | 8/1994 | Breneman et al. |
| 5,348,620 A | 9/1994 | Hermans et al. |
| 5,353,521 A | 10/1994 | Orloff |
| 5,431,786 A | 7/1995 | Rasch et al. |
| 5,443,899 A | 8/1995 | Barcus et al. |
| 5,489,469 A | 2/1996 | Kobayashi et al. |

(Continued)

FOREIGN PATENT DOCUMENTS

| | | |
|---|---|---|
| CA | 2 370 380 A1 | 10/2000 |
| EP | 0 192 216 B1 | 6/1990 |
| EP | 0 217 032 B1 | 2/1992 |
| WO | WO 98/19013 A1 | 5/1998 |
| WO | WO 99/25393 A2 | 5/1999 |
| WO | WO 99/25745 A1 | 5/1999 |
| WO | WO 99/25748 A1 | 5/1999 |
| WO | WO 00/56959 A1 | 9/2000 |
| WO | WO 00/63295 A1 | 10/2000 |
| WO | WO 01/49937 A1 | 7/2001 |

(Continued)

OTHER PUBLICATIONS

U.S. Appl. No. 10/242,571, filed Sep. 11, 2002, by Thomas Gerard Shannon et al. for "Improved Method for Using Water Insoluble Chemical Additives With Pulp and Products Made by Said Method."

(Continued)

*Primary Examiner*—T. Zalukaeva
(74) *Attorney, Agent, or Firm*—Bryan R. Rosiejka

(57) ABSTRACT

An absorbent core comprising fluff pulp fiber treated with polysiloxane, wherein the absorbent core has a density of about 0.15 g/cm³ or greater and a Young's modulus of about 75 psi or less. The polysiloxane may comprise an amino-functional moiety. The absorbent core may comprise superabsorbent, and may be employed in a disposable absorbent product.

26 Claims, 5 Drawing Sheets

U.S. PATENT DOCUMENTS

| | | | |
|---|---|---|---|
| 5,492,759 A | 2/1996 | Eriksson et al. |
| 5,496,624 A | 3/1996 | Stelljes, Jr. et al. |
| 5,500,277 A | 3/1996 | Trokhan et al. |
| 5,501,768 A | 3/1996 | Hermans et al. |
| 5,514,523 A | 5/1996 | Trokhan et al. |
| 5,547,541 A | 8/1996 | Hansen et al. |
| 5,554,467 A | 9/1996 | Trokhan et al. |
| 5,558,873 A | 9/1996 | Funk et al. |
| 5,566,724 A | 10/1996 | Trokhan et al. |
| 5,598,642 A | 2/1997 | Orloff et al. |
| 5,598,643 A | 2/1997 | Chuang et al. |
| 5,624,790 A | 4/1997 | Trokhan et al. |
| 5,628,876 A | 5/1997 | Ayers et al. |
| 5,637,194 A | 6/1997 | Ampulski et al. |
| 5,656,132 A | 8/1997 | Farrington, Jr. et al. |
| 5,693,411 A | 12/1997 | Hansen et al. |
| 5,695,868 A | 12/1997 | McCormack |
| 5,772,845 A | 6/1998 | Farrington, Jr. et al. |
| 5,785,813 A | 7/1998 | Smith et al. |
| 5,814,188 A | 9/1998 | Vinson et al. |
| 5,843,056 A | 12/1998 | Good et al. |
| 5,928,470 A | 7/1999 | Shannon |
| 5,935,383 A | 8/1999 | Sun et al. |
| 5,981,689 A | 11/1999 | Mitchell et al. |
| 5,986,166 A | 11/1999 | Mukaida et al. |
| 6,054,020 A | 4/2000 | Goulet et al. |
| 6,072,101 A | 6/2000 | Beihoffer et al. |
| 6,087,448 A | 7/2000 | Mitchell et al. |
| 6,096,169 A | 8/2000 | Hermans et al. |
| 6,103,063 A | 8/2000 | Oriaran et al. |
| 6,110,533 A | 8/2000 | Cote et al. |
| 6,117,525 A | 9/2000 | Trokhan et al. |
| 6,121,409 A | 9/2000 | Mitchell et al. |
| 6,143,135 A | 11/2000 | Hada et al. |
| 6,149,934 A | 11/2000 | Krzysik et al. |
| 6,159,591 A | 12/2000 | Beihoffer et al. |
| 6,168,852 B1 | 1/2001 | Smith, III et al. |
| 6,194,631 B1 | 2/2001 | Mitchell et al. |
| 6,222,091 B1 | 4/2001 | Beihoffer et al. |
| 6,224,714 B1 | 5/2001 | Schroeder et al. |
| 6,228,506 B1 | 5/2001 | Hosatte et al. |
| 6,231,719 B1 | 5/2001 | Garvey et al. |
| 6,235,155 B1 | 5/2001 | Schroeder et al. |
| 6,235,965 B1 | 5/2001 | Beihoffer et al. |
| 6,261,580 B1 | 7/2001 | Lehrter et al. |
| 6,270,893 B1 | 8/2001 | Young, Sr. et al. |
| 6,274,667 B1 | 8/2001 | Shannon et al. |
| 6,287,418 B1 | 9/2001 | Schroeder et al. |
| 6,300,259 B1 | 10/2001 | Westland et al. |
| 6,342,298 B1 | 1/2002 | Evans et al. |
| 6,365,667 B1 | 4/2002 | Shannon et al. |
| 6,376,072 B1 | 4/2002 | Evans et al. |
| 6,379,498 B1 | 4/2002 | Burns et al. |
| 6,392,116 B1 | 5/2002 | Beihoffer et al. |
| 6,423,183 B1 | 7/2002 | Goulet et al. |
| 6,432,268 B1 | 8/2002 | Burghardt |
| 6,432,270 B1 | 8/2002 | Liu et al. |
| 6,458,343 B1 | 10/2002 | Zeman et al. |
| 6,461,553 B1 | 10/2002 | Hansen et al. |
| 6,509,512 B1 | 1/2003 | Beihoffer et al. |
| 6,511,580 B1 | 1/2003 | Liu |
| 6,514,383 B1 | 2/2003 | Liu et al. |
| 6,521,339 B1 | 2/2003 | Hansen et al. |
| 6,552,245 B1 | 4/2003 | Roessler et al. |
| 6,555,502 B1 | 4/2003 | Beihoffer et al. |
| 6,582,560 B2 | 6/2003 | Runge et al. |
| 6,599,393 B1 | 7/2003 | Liu |
| 6,599,394 B1 | 7/2003 | Liu et al. |
| 6,632,904 B2 | 10/2003 | Schroeder et al. |
| 6,896,766 B2 | 5/2005 | Sarbo et al. |
| 6,916,402 B2 | 7/2005 | Shannon et al. |
| 6,936,136 B2 | 8/2005 | Shannon et al. |
| 2001/0001312 A1 | 5/2001 | Mitchell et al. |
| 2001/0007064 A1 | 7/2001 | Mitchell et al. |
| 2001/0029358 A1 | 10/2001 | Beihoffer et al. |
| 2001/0037100 A1* | 11/2001 | Shanklin ................ 604/358 |
| 2001/0044612 A1 | 11/2001 | Beihoffer et al. |
| 2002/0007166 A1 | 1/2002 | Mitchell et al. |
| 2002/0015846 A1 | 2/2002 | Evans et al. |
| 2002/0162243 A1 | 11/2002 | Runge et al. |
| 2003/0014027 A1 | 1/2003 | Beihoffer et al. |
| 2003/0124171 A1 | 7/2003 | Sun et al. |
| 2003/0131962 A1 | 7/2003 | Lindsay et al. |
| 2003/0208173 A1* | 11/2003 | Lagerstedt-Eidrup et al. ................ 604/367 |
| 2004/0023579 A1 | 2/2004 | Kainth et al. |
| 2004/0045687 A1 | 3/2004 | Shannon et al. |
| 2004/0074622 A1 | 4/2004 | Liu et al. |
| 2004/0084164 A1 | 5/2004 | Shannon et al. |
| 2004/0084165 A1 | 5/2004 | Shannon et al. |
| 2004/0086726 A1 | 5/2004 | Moline et al. |
| 2004/0100376 A1 | 5/2004 | Lye et al. |
| 2004/0118531 A1 | 6/2004 | Shannon et al. |
| 2004/0144507 A1 | 7/2004 | Shannon et al. |
| 2004/0163785 A1 | 8/2004 | Shannon et al. |
| 2004/0234804 A1 | 11/2004 | Liu et al. |
| 2004/0253890 A1 | 12/2004 | Ostgard et al. |
| 2005/0136265 A1 | 6/2005 | Liu et al. |
| 2005/0136759 A1 | 6/2005 | Shannon et al. |

FOREIGN PATENT DOCUMENTS

| | | |
|---|---|---|
| WO | WO 02/10032 A2 | 2/2002 |
| WO | WO 02/34184 A1 | 5/2002 |
| WO | WO 02/072951 A2 | 9/2002 |
| WO | WO 02/077048 A2 | 10/2002 |
| WO | WO 02/081819 A1 | 10/2002 |
| WO | WO 03/018671 A1 | 3/2003 |
| WO | WO 03/037392 A1 | 5/2003 |
| WO | WO 2004/044327 A1 | 5/2004 |
| WO | WO 2004/050995 A1 | 6/2004 |
| WO | WO 2004/101684 A1 | 11/2004 |

OTHER PUBLICATIONS

U.S. Appl. No. 10/289,557, filed Nov. 6, 2002, by David A. Moline et al. for "Soft Tissue Hydrophilic Tissue Products Containing Polysiloxane and Having Unique Absorbent Properties."

U.S. Appl. No. 10/289,809, filed Nov. 6, 2002, by Thomas Gerard Shannon et al. for "Soft Tissue Products Containing Polysiloxane Having a High Z-Directional Gradient."

U.S. Appl. No. 10/289,835, filed Nov. 6, 2002, by Thomas Gerard Shannon et al. for "Soft Tissue Products Containing Selectively Treated Fibers."

U.S. Appl. No. 10/325,484, filed Dec. 19, 2002, by Thomas Gerard Shannon et al. for "Tissue Products Having Uniformly Deposited Hydrophobic Additives and Controlled Wettability."

U.S. Appl. No. 10/325,493, filed Dec. 20, 2002, by Benjamin Sarbo et al. for "Paper Wiping Products Treated With a Hydrophobic Additive."

U.S. Appl. No. 10/328,705, filed Dec. 23, 2002, by Thomas Gerard Shannon et al. for "Process for Bonding Chemical Additives on to Substrates Containing Cellulosic Materials and Products Thereof."

U.S. Appl. No. 10/335,133, filed Dec. 31, 2002, by Thomas Gerard Shannon et al. for "Amino-Functionalized Pulp Fibers."

U.S. Appl. No. 10/371,546, filed Feb. 20, 2003, by Thomas Gerard Shannon et al. for "Paper Wiping Products Treated With a Polysiloxane Composition."

U.S. Appl. No. 10/441,143, filed May 19, 2003, by Kou-Chang Liu et al. for "Single Ply Tissue Products Surface Treated With a Softening Agent."

U.S. Appl. No. 10/461,942, filed Jun. 13, 2003, by Estelle A. Ostgard et al. for "Fibers With Lower Edgewise Compression Strength and Sap Containing Composites Made From the Same."

U.S. Appl. No. 10/741,036, filed Dec. 19, 2003, by Thomas Gerard Shannon et al. for "Tissue Sheets Containing Multiple Polysilxoanes and Having Regions of Varying Hydrophobicity."

U.S. Appl. No. 10/741,040, filed Dec. 19, 2003, by Thomas Gerard Shannon et al. for "Hydrophilic Fibers Containing Substantive Polysiloxanes and Tissue Products Made Therefrom."

U.S. Appl. No. 10/741,041, filed Dec. 19, 2003, by Kou-Chang Liu et al. for "Soft Tissue Hydrophilic Tissue Products Containing Polysiloxane and Having Unique Absorbent Properties."

TAPPI Official Test Method T 402 om-93, "Standard Conditioning and Testing Atmospheres For Paper, Board, Pulp Handsheets, and Related Products," published by the TAPPI Press, Atlanta, Georgia, revised 1993, pp. 1-3.

TAPPI Official Test Method T 410 om-98, "Grammage of Paper and Paperboard (Weight Per Unit Area)," published by the TAPPI Press, Atlanta, Georgia, revised 1998, pp. 1-5.

TAPPI Official Test Method T 411 om-89, "Thickness (Caliper) of Paper, Paperboard, and Combined Board," published by the TAPPI Press, Atlanta, Georgia, revised 1989, pp. 1-3.

TAPPI Official Test Method T 530 pm-89, "Size Test for Paper By Ink Resistance (Hercules Method)," published by the TAPPI Press, Atlanta, Georgia, revised 1989, pp. 1-5.

Foulger, M. et al., "New Technology to Apply Starch and Other Additives," *Pulp & Paper* Canada, vol. 100, No. 2, 1999, pp. 24-25.

* cited by examiner

HIGHLY WETTABLE—HIGHLY FLEXIBLE FLUFF FIBERS AND DISPOSABLE ABSORBENT PRODUCTS MADE OF THOSE

BACKGROUND OF THE INVENTION

Disposable absorbent products such as infant diapers, diaper-pants, training pants, feminine care pads and adult incontinence pads/garments are complex products designed to absorb insults of various bodily exudates. These types of absorbent products include multiple components, are made on high speed production lines, need to be cost affordable and most importantly, must perform their intended function. In order to be of the quality expected by consumers, individual absorbent products need to include a complete set of the individual components (e.g. an absorbent core, pair of fasteners, pair of leg elastics, pair of containment flaps, etc.). Manufacturing systems have been developed that bring all of the components together in one "web" of materials from which individual absorbent products are formed. The quality of the individual absorbent products is controlled so that each product has the intended components and the components are properly attached to and aligned with each other, with some tolerance for manufacturing variability.

Disposable absorbent products are typically constructed of multiple nonwoven material components. For example, disposable absorbent products may include a bodyside liner (also known as a topsheet) that contacts the wearer's skin in use, an absorbent core and an outer cover (also known as a backsheet) that is typically liquid impermeable. In addition, disposable absorbent products may include components such as leg elastics, waist elastics, containment flaps, front waist ear portions, back waist ear portions and fastening systems for improving the fit and containment of the products. In order to form the finished absorbent product, the various components are placed in desired relationship to each other and, where necessary, the components are attached to each other using methods known in the art. The "chassis" of a disposable absorbent product typically refers to the combination of the bodyside liner, absorbent core and outer cover components. The chassis of an absorbent product may include two longitudinal edges, that generally define the length of an article, and two lateral edges, that generally define the waist edges and width of the absorbent product.

The fluff pulp fibers used in the absorbent core of an absorbent product provide mechanical strength and integrity to the absorbent core, and ultimately, to the absorbent product. In addition, the fluff pulp fibers provide the necessary surface energy to distribute the insulting exudates within the absorbent product. Current treated and non-treated fluff pulp fibers, when used with superabsorbent materials in an air-formed absorbent product, creates a stiff, rigid absorbent core that is typically poorly conformable to the body of the wearer and/or does not interact with the other components of the absorbent product to provide an absorbent product having adequate comfort and/or functionality.

While various components of disposable absorbent products have been altered, modified, or manipulated to provide improved products, fluff pulp fibers have not been optimized for flexibility and absorbency. Consequently, there remains a need in the area of disposable absorbent products for absorbent cores comprising fluff pulp fibers that provide improved flexibility (and consequently, improved conformability) and absorbency of such products. There also remains a need for a fluff pulp fiber treatment to provide absorbent fluff pulp fibers having a low dry stiffness capable of providing a conformable disposable absorbent product when incorporated in the absorbent core of the disposable absorbent product.

SUMMARY OF THE INVENTION

As described herein, absorbent articles typically include three primary components: a bodyside liner, an absorbent core and an outer cover. The "chassis" typically includes the outer cover, the bodyside liner or both the outer cover and the bodyside liner. Typically, the two-dimensional area of the absorbent core is somewhat less than the entire area of the chassis. The bodyside liner and outer cover materials are generally contiguous and together, they surround the absorbent core. Many absorbent articles have systems for the fastening of the absorbent product about or adjacent a wearer.

The present invention includes a disposable absorbent product that has a longitudinal direction and a lateral direction. The longitudinal direction may correspond to the "machine direction" of the article, which is the direction in which the absorbent product is manufactured. The lateral direction may be generally perpendicular to the longitudinal direction. Typically, the longitudinal dimension of the disposable absorbent product is longer than the lateral dimension. The disposable absorbent product may also include an outer cover and the outer cover may have a longitudinal edge. The longitudinal edge may be generally aligned with the longitudinal direction of the absorbent product. The outer cover may also include an outer cover material. The outer cover material may be a laminate of a nonwoven material and a liquid impermeable film material. Either or both of the nonwoven material and the film material may be extensible, stretchable or elastic. The disposable absorbent product may also include an ear portion that extends laterally outward from the longitudinal edge of the outer cover. Disposable absorbent product such as infant diapers, diaper-pants and training pants typically include a front waist region, a back waist region and a crotch region that interconnects the front waist region and the back waist region.

One embodiment of the present invention may be an absorbent core comprising fluff pulp fiber wherein the absorbent core has a density of about 0.15 g/cm$^3$ or greater and a Young's modulus of about 75 psi or less.

These aspects and additional aspects of the invention will be described in greater detail herein. Further, it is to be understood that both the foregoing general description and the following detailed description are exemplary and are intended to provide further explanation of the invention claimed. The accompanying drawings, that are incorporated in and constitute part of this specification, are included to illustrate and provide a further understanding of the disposable absorbent articles of the invention. Together with the description, the drawings serve to explain various aspects of the invention.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

DETAILED DESCRIPTION OF THE INVENTION

Figure 1:
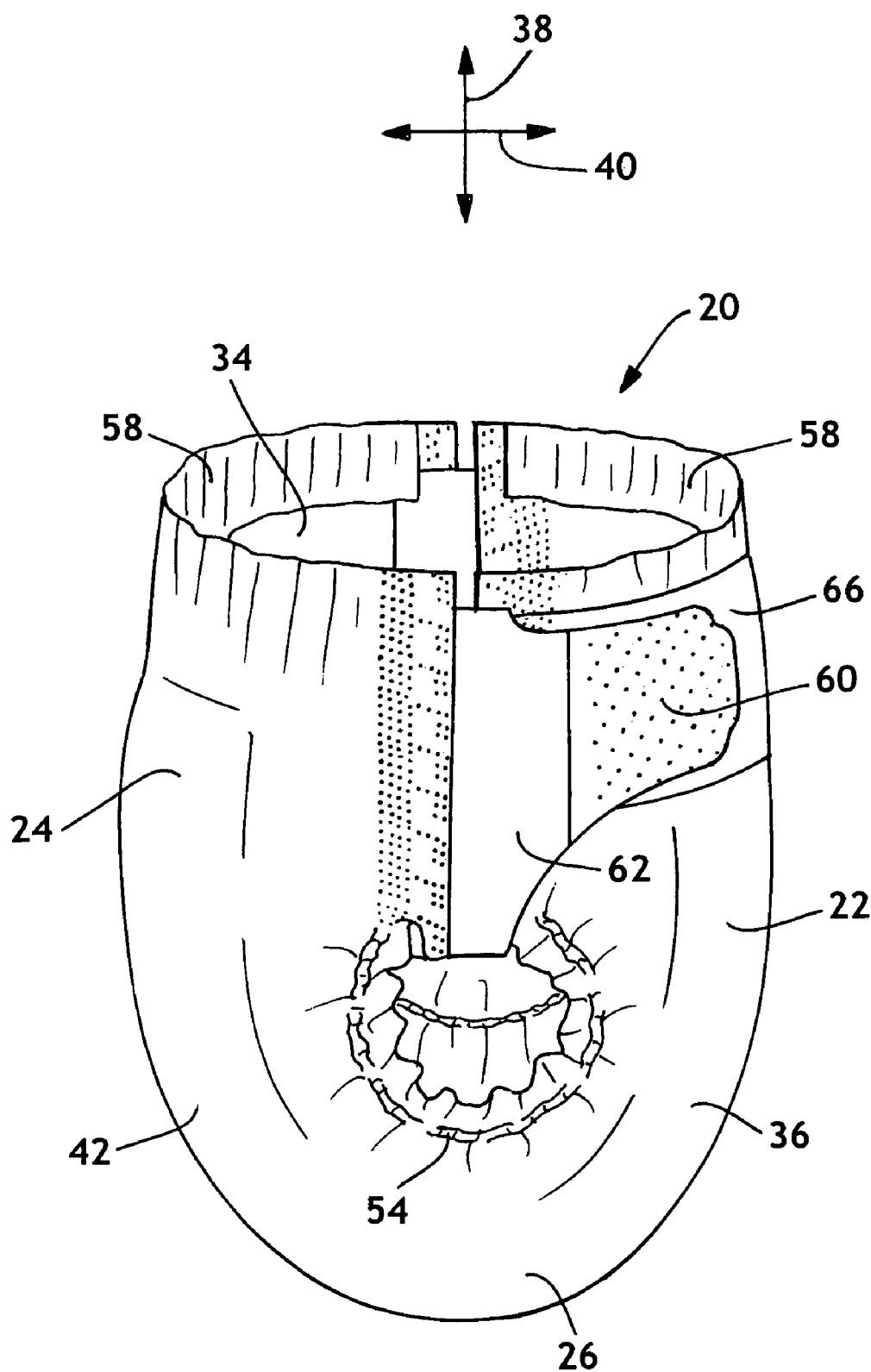
FIG. 1 representatively shows a perspective view of an example of a disposable absorbent article (an infant diaper) of the present invention.

The disclosure of a disposable absorbent product of the present invention will be expressed in terms of its various components, elements, constructions, configurations, arrangements and other features that may also be individually or collectively be referenced by the term, "aspect(s)" of the invention, or other similar terms. It is contemplated that the various forms of the disclosed invention may incorporate one or more of its various features and aspects, and that such features and aspects may be employed in any desired, operative combination thereof.

It should also be noted that, when employed in the present disclosure, the terms "comprises", "comprising" and other derivatives from the root term "comprise" are intended to be open-ended terms that specify the presence of any stated ingredients, features, elements, integers, steps, components, or groups and are not intended to preclude the presence or addition of one or more other ingredients, features, elements, integers, steps, components, groups, or combinations thereof.

The present invention is directed to solving problems related to fluff pulp fibers and disposable absorbent products comprising such fluff pulp fibers. Additionally, the present invention is directed to improving the flexibility and absorbency of fluff pulp fibers incorporated into absorbent cores of disposable absorbent products. This detailed description of the present invention will include a description of a representative fluff pulp fiber and disposable absorbent product including the various components of such products. The description of the representative disposable absorbent product will also include a description of the features encompassed by the present invention.

The particular structure of the polysiloxanes of the present invention may provide the desired product properties to the fluff pulp fibers and disposable absorbent products. Polysiloxanes encompass a very broad class of compounds. They are characterized in having a backbone structure:

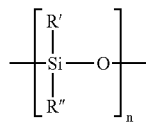

where R' and R" may be a broad range of organo and non-organo groups including mixtures of such groups and where n is an integer $\geq 2$. These polysiloxanes may be linear, branched, or cyclic. They may include a wide variety of polysiloxane copolymers containing various compositions of functional groups, hence, R' and R" actually may represent many different types of groups within the same polymer molecule. The organo or non-organo groups may be capable of reacting with fluff pulp fibers to covalently, ionically or hydrogen bond the polysiloxane to the fluff pulp fibers. These functional groups may also be capable of reacting with themselves to form crosslinked matrixes with the fluff pulp fibers. The scope of the present invention should not be construed as limited by particular polysiloxane structures so long as that polysiloxane structure delivers the aforementioned product benefits to the fluff pulp fibers and/or the disposable absorbent product.

The term "polydialkylsiloxane" as used herein refers to the portion of the polysiloxane molecule as defined above wherein R' and R" are $C_1$-$C_{30}$ aliphatic hydrocarbon groups. In one embodiment of the present invention, R' and R" may be methyl groups forming so called polydimethylsiloxane units. While not wishing to be bound by theory, the polydialkylsiloxane units may be capable of increasing the softness of fluff pulp fibers and/or disposable absorbent products comprising polysiloxane treated fluff pulp fibers. Functionalized polysiloxanes containing polydialkylsiloxane units may be used for the purposes of the present invention. A variety of functional groups may be present on the polysiloxane polymer in addition to the dialkylsiloxane units. A combination of polysiloxanes may also be used to create the desired fluff pulp fibers and/or disposable absorbent products.

The polysiloxane may be delivered to the fluff pulp fiber or the disposable absorbent product in a variety of forms including but not limited to an aqueous emulsion or dispersion, a solution in an organic fluid or non-organic fluid medium, or as a neat polysiloxane containing no added solvents, emulsifiers, or other agents.

A specific class of hydrophobic polysiloxanes suitable for use in the present invention to be blended with the hydrophilic polysiloxane may have the general formula:

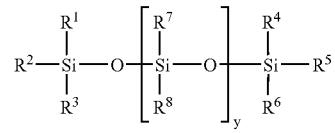

wherein the $R^1$-$R^8$ moieties may be independently any organofunctional group including $C_1$ or higher alkyl groups, aryl groups, ethers, polyethers, polyesters, amines, imines, amides, or other functional groups including the alkyl and alkenyl analogues of such groups and y is an integer >1. Specifically, the $R^1$-$R^8$ moieties may be independently any $C_1$ or higher alkyl group including mixtures of the alkyl groups. Examples of polysiloxanes that may be useful in the present invention are those in the DC-200 fluid series and HMW-2200, manufactured and sold by Dow Corning, Inc., located in Midland, Mich.

Additional examples of hydrophobic polysiloxanes that are known in the art and may be well suited for use in the present invention are the so called amino-functional polysiloxanes. These amino-functional polysiloxanes having the following general structure may be useful in the present invention:

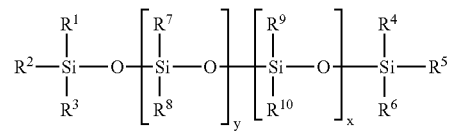

wherein, x and y are integers >0. The mole ratio of x to (x+y) may be from about 0.005 percent to about 25 percent. The $R^1$-$R^9$ moieties may be independently any organofunctional group including $C_1$ or higher alkyl groups, aryl groups, ethers, polyethers, polyesters, amines, imines, amides, or other functional groups including the alkyl and alkenyl analogues of such groups. The $R^{10}$ moiety may be an amino-functional moiety including but not limited to primary amine, secondary amine, tertiary amines, quaternary amines, unsubstituted amides and mixtures thereof. In one embodiment, the $R^{10}$ moiety may comprise at least one amine group per constituent or two or more amine groups per substituent, separated by a linear or branched alkyl chain of $C_1$ or greater. Examples of some polysiloxanes that may be useful in the present invention include, but are not limited to, DC 2-8220, DC-8175 and DC-8182 commercially available from Dow Corning, Inc., located in Midland, Mich., Y-14344 commercially available from Crompton, Corp., located at Greenwich, Conn. and AF-2340 commercially available from Wacker, Inc., Adrian, Mich.

The polysiloxane treated fluff pulp fibers and/or disposable absorbent products of the present invention incorporate at least one hydrophilic polysiloxane. Such polysiloxanes may be incorporated wholly or in part with other functional polysiloxanes to generate the required hydrophilic properties of the fluff pulp fibers and/or disposable absorbent products. One common class of hydrophilic polysiloxanes is the so called polyether polysiloxanes. Such polysiloxanes generally have the following structure:

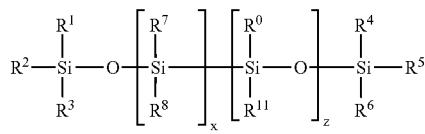

wherein, z is an integer >0 and x is an integer ≧0. The mole ratio of x to (x+z) may be from about 0 percent to about 95 percent. The $R^0$-$R^9$ moieties may be independently any organofunctional group including a $C_1$ or higher alkyl or aryl group or mixtures of such groups. $R^{11}$ may be a polyether functional group having the generic formula: —$R^{12}$—($R^{13}$—O)$_a$—($R^{14}$O)$_b$—$R^{15}$, wherein $R^{12}$, $R^{13}$, and $R^{14}$ may be independently $C_{1-4}$ alkyl groups, linear or branched; $R^{15}$ may be H or a $C_{1-30}$ alkyl group; and, "a" and "b" are integers of from about 1 to about 100, more specifically from about 5 to about 30. An example of a commercially available polyethers polysiloxane is DC-1248 available from Dow Corning. While these polysiloxanes are broadly taught in the art and used in combination with hydrophobic polysiloxanes their use is limited by the restrictions noted previously.

A class of functionalized hydrophilic polysiloxanes particularly suitable for use in the present invention are polyether polysiloxanes that include an additional functional group capable of substantively affixing the hydrophilic polysiloxane to the fluff pulp fibers. Thus, the hydrophilic polysiloxane is retained by the polysiloxane treated fluff pulp fibers during wet laid papermaking processes. Such polysiloxanes may generally have the following structure:

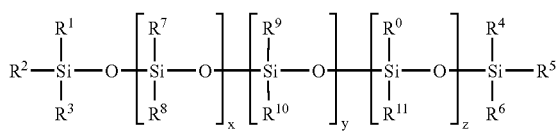

wherein, z is an integers >0, x and y are integers ≧0. The mole ratio of x to (x+y+z) may be from about 0 percent to about 95 percent. The ratio of y to (x+y+z) may be from about 0 percent to about 40%. The $R^0$-$R^9$ moieties may be independently any organofunctional group including $C_1$ or higher alkyl groups, aryl groups, ethers, polyethers, polyesters or other functional groups including the alkyl and alkenyl analogues of such groups. The $R^{10}$ moiety is a moiety capable of substantively affixing the polysiloxane to the cellulose. In a specific embodiment the $R^{10}$ moiety is an amino-functional moiety including, but not limited to, primary amine, secondary amine, tertiary amines, quaternary amines, unsubstituted amides, and mixtures thereof. An exemplary $R^{10}$ amino functional moiety may contain one amine group per constituent or two or more amine groups per substituent, separated by a linear or branched alkyl chain of $C^1$ or greater. $R^{11}$ may be a polyether-functional group having the generic formula: —$R^{12}$—($R^{13}$—O)$_a$—($R^{14}$O)$_b$—$R^{15}$, wherein $R^{12}$, $R^{13}$, and $R^{14}$ may be independently $C_{1-4}$ alkyl groups, linear or branched; $R^{15}$ may be H or a $C_{1-30}$ alkyl group; and, "a" and "b" are integers of from about 1 to about 100, more specifically from about 5 to about 30.

Examples of amino-functional polysiloxanes that may be useful in the present invention include the polysiloxanes provided under the trade designation of Wetsoft CTW family manufactured and sold by Wacker, Inc., located Adrian, Mich. Other examples of such polysiloxanes may be found in U.S. Pat. No. 6,432,270, issued on Aug. 13, 2002 to Liu, et al., U.S. Pat. No. 6,599,393 issued on Jun. 29, 2003 to Liu, et al., U.S. Pat. No. 6,511,580 issued on Jan. 28, 2003 to Liu, U.S. Pat. No. 6,514,383 issued on Feb. 4, 2003 to Liu, U.S. Pat. No. 6,235,155 issued on May 22, 2001 to Schroeder, et al., and U.S. Pat. No. 6,632,904 issued on Oct. 14, 2003 to Schroeder, et al., the disclosures of which are incorporated herein by reference to the extent that they are non-contradictory herewith. In another aspect of the present invention, the moiety capable of affixing the polysiloxane substantively to the pulp fiber may be incorporated into the hydrophilic segment of the polysiloxane polymer or on one of the other $R^0$-$R^{11}$ moieties. In such case, the value of y in the above structure for the hydrophilic polysiloxane may be 0.

The total amount of polysiloxane in the polysiloxane treated fluff pulp fibers may vary. However, the amount of the total polysiloxane present in the treated fluff pulp fibers may range from about 0.05% to about 5.0% by weight of dry fiber, more specifically from about 0.05% to about 2.5% by weight of dry fiber, more specifically from about 0.05% to about 0.5% by weight of dry fiber, and still more specifically from about 0.05% to about 0.25% by weight of dry fiber.

The total amount of polysiloxane in the absorbent cores comprising the polysiloxane treated fluff pulp fibers may vary depending upon other things, including the amount of treated and untreated fluff pulp fibers and/or layers of the polysiloxane treated fluff pulp fibers present in the absorbent core of the disposable absorbent product as well as other components of the absorbent core. However, the amount of total polysiloxane present in the absorbent core of the present invention may range from about 0.02% to about 2.0% by weight of dry fluff pulp fibers, more specifically from about 0.02% to about 1.0% by weight of dry fluff pulp fibers, and still more specifically from about 0.02% to about 0.3% by weight of dry fluff pulp fibers, and still more specifically from about 0.02% to about 0.1% by weight of dry fluff pulp fibers.

The polysiloxane treated fluff pulp fibers and absorbent cores of the disposable absorbent products comprising the polysiloxane treated fluff pulp fibers of the present invention have improved dry flexibility properties. The dry flexibility of the polysiloxane treated fluff pulp fibers and/or absorbent cores of the disposable absorbent products comprising the polysiloxane treated fluff pulp fibers may be determined by rigidity. The rigidity (hereinafter defined) for polysiloxane treated fluff pulp fibers and/or absorbent cores of disposable absorbent products comprising the polysiloxane treated fluff pulp fibers of the present invention may be measured by a Young Modulus (E) of about 0.5 psi to 2000 psi more specifically about 5 psi to 1000 psi, still more specifically about 40 psi to 800 psi, and still more specifically about 100 psi to 500 psi.

The polysiloxane treated fluff pulp fibers and absorbent cores of the disposable absorbent products comprising the polysiloxane treated fluff pulp fibers of the present invention have good absorbency properties despite the high level of polydialkylsiloxane on the treated fluff pulp fibers. The absorbency of the polysiloxane treated fluff pulp fibers and/or absorbent cores of the disposable absorbent products comprising the polysiloxane treated fluff pulp fibers may be determined by the $2^{nd}$ Intake Rate (IR). The $2^{nd}$ IR test (hereinafter defined) for polysiloxane treated fluff pulp fibers and/or absorbent cores of disposable absorbent products comprising the polysiloxane treated fluff pulp fibers of the present invention may be about 0.2 mL/S to 6 about mL/S more specifically about 0.5 mL/S to about 5 mL/S, still more specifically about 1 mL/S to about 5 mL/S, and still more specifically about 2 mL/S to about 5 mL/S.

The ratio of substantive hydrophilic polysiloxane to hydrophobic polysiloxane may be varied so long as the desired disposable absorbent product properties are met. In one embodiment, the ratio of the substantive hydrophilic polysiloxane to hydrophobic polysiloxane used as a treatment may range from about 9.5:0.5 to about 0.5:9.5. In another embodiment of the present invention, the ratio of the substantive hydrophilic polysiloxane to hydrophobic polysiloxane may range from about 8:2 to about 2:8. In still another embodiment of the present invention, the ratio of the substantive hydrophilic polysiloxane to hydrophobic polysiloxane may range from about 2:1 to about 1:2.

While not wishing to be bound by theory, the flexibility benefits that polysiloxanes deliver to fluff pulp fiber and/or the absorbent cores of the disposable absorbent products comprising the polysiloxane treated fluff pulp fibers of the present invention is believed to be, in part, related to the molecular weight of the polysiloxane. Viscosity is often used as an indication of molecular weight of the polysiloxane as exact number or weight average molecular weights are often difficult to determine. The viscosity of the polysiloxanes of the present invention at 25° C. may be about 0.5 centipoise to about 50,000 centipoise, more specifically about 5 centipoise to about 5,000 centipoise, and most specifically about 50 centipoise to about 5,000 centipoise. The term "viscosity" as referred to herein refers to the viscosity of the neat polysiloxane itself and not to the viscosity of an emulsion if so delivered. It should also be understood that the polysiloxanes of the present invention may be delivered as solutions containing diluents. Such diluents may lower the viscosity of the solution below the limitations set above, however, the efficacious part of the polysiloxane should conform to the viscosity ranges given above. Examples of such diluents may include, but is not limited to: oligomeric and cyclo-oligomeric polysiloxanes such as octamethylcyclotetrasiloxane, octamethyltrisiloxane, decamethylcyclopentasiloxane, decamethyltetrasiloxane and the like, including mixtures of these compounds.

The level of total polysiloxane in the polysiloxane treated fluff pulp fibers, dry lap sheets comprising the polysiloxane treated fluff pulp fibers, webs comprising the treated fluff pulp fibers, and/or absorbent cores of the disposable absorbent products comprising the polysiloxane treated fluff pulp fibers may be determined by any method known in the art. If the particular polysiloxane applied to the polysiloxane treated fluff pulp fibers is known, the total amount of polysiloxane may be measured by converting the dialkylpolysiloxane component of the polysiloxane to the corresponding dialkyldiflouro silane using $BF_3$ followed by GC quantification of the dialkylpolysiloxane as described herein. The amount of polydialkylsiloxane in the polysiloxane treated fluff pulp fibers, dry lap sheet comprising the treated fluff pulp fibers, web comprising the fluff pulp fibers, and/or the absorbent core is determined using the $BF_3$-GC method as described herein.

The polysiloxane treatment composition may be applied to the fluff pulp fibers, dry lap sheets comprising the fluff pulp fibers, webs comprising the fluff pulp fibers, and/or absorbent cores comprising the fluff pulp fibers according to various methods with the exact method not being overly critical to the present invention.

The topical application of the polysiloxane treatment composition to the fluff pulp fibers, dry lap sheets comprising the fluff pulp fibers, webs comprising the fluff pulp fibers, and/or absorbent cores comprising the fluff pulp fibers may be done via any method known in the art including but not limited to:

- Contact printing methods such as gravure, offset gravure or flexographic.
- A spray applied to the fluff pulp fibers, dry lap sheets comprising fluff pulp fibers, webs comprising the fluff pulp fibers, and/or absorbent cores comprising fluff pulp fibers. For example, spray nozzles may be mounted over a moving web of fluff pulp fibers during the air-form process to apply a desired dose of polysiloxane treatment composition to the web. Nebulizers may also be used to apply a light mist to a surface of such a web comprising fluff pulp fibers.
- Non-contact printing methods such as ink jet printing, digital printing of any kind, and the like.
- Coating onto one or both surfaces of the fluff pulp fibers, dry lap sheets comprising fluff pulp fibers, webs comprising the fluff pulp fibers, and/or absorbent cores comprising fluff pulp fibers, such as blade coating, air knife coating, short dwell coating, cast coating, and the like.
- Extrusion from a die head such as UFD spray tips, such as available from ITW-Dynatec of Henderson, Tenn., of the polysiloxane treatment composition in the form of a solution, a dispersion or emulsion, or a viscous mixture.
- Impregnation of the fluff pulp fibers, dry lap sheets comprising fluff pulp fibers, webs comprising the fluff pulp fibers, and/or absorbent cores comprising fluff pulp fibers with a solution or slurry, wherein the polysiloxane treatment composition penetrates a significant distance into the thickness of the fluff pulp fibers, dry lap sheets comprising fluff pulp fibers, webs comprising the fluff pulp fibers, and/or absorbent cores comprising fluff pulp fibers, such as more than about 30% of the thickness, more specifically at least about 60% of the thickness, and most specifically at least about 90% of the thickness, including completely penetrating the fluff pulp fibers, dry lap sheets comprising fluff pulp fibers, webs comprising the fluff pulp fibers, and/or absorbent cores comprising fluff pulp fibers throughout the full extent of its thickness. One useful method for impregnation may be the Hydra-Sizer® system, produced by Black Clawson Corp., Watertown, N.Y., as described in "New Technology to Apply Starch and Other Additives," Pulp and Paper Canada, 100(2): T42-T44 (February 1999). This system consists of a die, an adjustable support structure, a catch pan, and an additive supply system. A thin curtain of descending liquid or slurry is created which contacts the moving fluff pulp fibers, dry lap sheets comprising fluff pulp fibers, webs comprising the fluff pulp fibers, and/or absorbent cores comprising fluff pulp fibers beneath it. Wide ranges of applied doses of the coating material are said to be achievable with good runnability.

Foam application of the polysiloxane treatment composition to the fluff pulp fibers, dry lap sheets comprising fluff pulp fibers, webs comprising the fluff pulp fibers, and/or absorbent cores comprising fluff pulp fibers (e.g., foam finishing), either for topical application or for impregnation of the composition into it under the influence of a pressure differential (e.g., vacuum-assisted impregnation of the foam). Principles of foam application of additives such as binder agents are described in U.S. Pat. No. 4,297,860, issued on Nov. 3, 1981 to Pacifici et al. and U.S. Pat. No. 4,773,110, issued on Sep. 27, 1988 to G. J. Hopkins, the disclosures of both which are herein incorporated by reference to the extent that they are non-contradictory herewith.

Application of the polysiloxane treatment composition by spray or other means to a moving belt or fabric which in turn contacts the fluff pulp fibers, dry lap sheets comprising fluff pulp fibers, webs comprising the fluff pulp fibers, and/or absorbent cores comprising fluff pulp fibers to apply the chemical it, such as is disclosed in WO 01/49937 under the name of S. Eichhorn, published on Jun. 12, 2001.

While the method of application of the present invention may be accomplished by any suitable means known in the art, it has been surprisingly found that when applied under certain conditions, specifically when applied as a neat fluid, the polysiloxane blends of a polysiloxane treatment composition of the present invention may show improved hydrophilicity over the hydrophilic polysiloxane treatment composition alone. While not wishing to be bound by theory it is hypothesized that when combined as neat fluids the viscosity of the polysiloxane blend of a polysiloxane treatment composition is increased substantially. The increased viscosity of the polysiloxane blend of a polysiloxane treatment composition may cause reduced spreading of the polysiloxane treatment compositions across the surface and less tendency of the polysiloxane to reorient under thermal aging conditions. Hence, such polysiloxane blends of polysiloxane treatment compositions may actually show improved hydrophilicity over even the hydrophilic polysiloxane treatment compositions.

When topically applied, the polysiloxane treatment composition may be applied to fluff pulp fibers, dry lap sheets comprising fluff pulp fibers, webs comprising the fluff pulp fibers, and/or absorbent cores comprising fluff pulp fibers so as to cover substantially the entire surface or may be applied in a pattern on the fluff pulp fibers, dry lap sheets comprising fluff pulp fibers, webs comprising the fluff pulp fibers, and/or absorbent cores comprising fluff pulp fibers. For example, the polysiloxane treatment composition may be applied to cover anywhere from about 20 percent to 100 percent of the surface area. The polysiloxane treatment composition may be applied to a single side or may be applied to both sides.

In one aspect of the present invention, the polysiloxane treatment composition may be applied uniformly over the x-y direction of the fluff pulp fibers, dry lap sheets comprising fluff pulp fibers, webs comprising the fluff pulp fibers, and/or absorbent cores comprising fluff pulp fibers in a manner that at least about 50%, more specifically at least about 60% and still more specifically at least about 70% of the x-y plane of any side upon which has polysiloxane applied. In a specific embodiment of the present invention, the polysiloxane treatment composition is applied to the surface of the fluff pulp fibers, dry lap sheets comprising fluff pulp fibers, webs comprising the fluff pulp fibers, and/or absorbent cores comprising fluff pulp fibers in a uniform pattern such that at least 75% of the treated surface is covered and such that the distance between treated and untreated areas does not exceed 0.5 mm. In another specific embodiment of the present invention, the polysiloxane treatment composition may be applied in the wet end of the process prior to the air-formed process to manufacture the fluff pulp fibers, dry lap sheets comprising fluff pulp fibers, webs comprising the fluff pulp fibers, and/or absorbent cores comprising fluff pulp fibers either by addition to a slurry of fluff pulp fibers in water or by addition as pretreated fluff pulp fibers as described in U.S. Pat. No. 6,582,560 issued to Runge, et. al., on Jun. 24, 2003.

Figure 3:
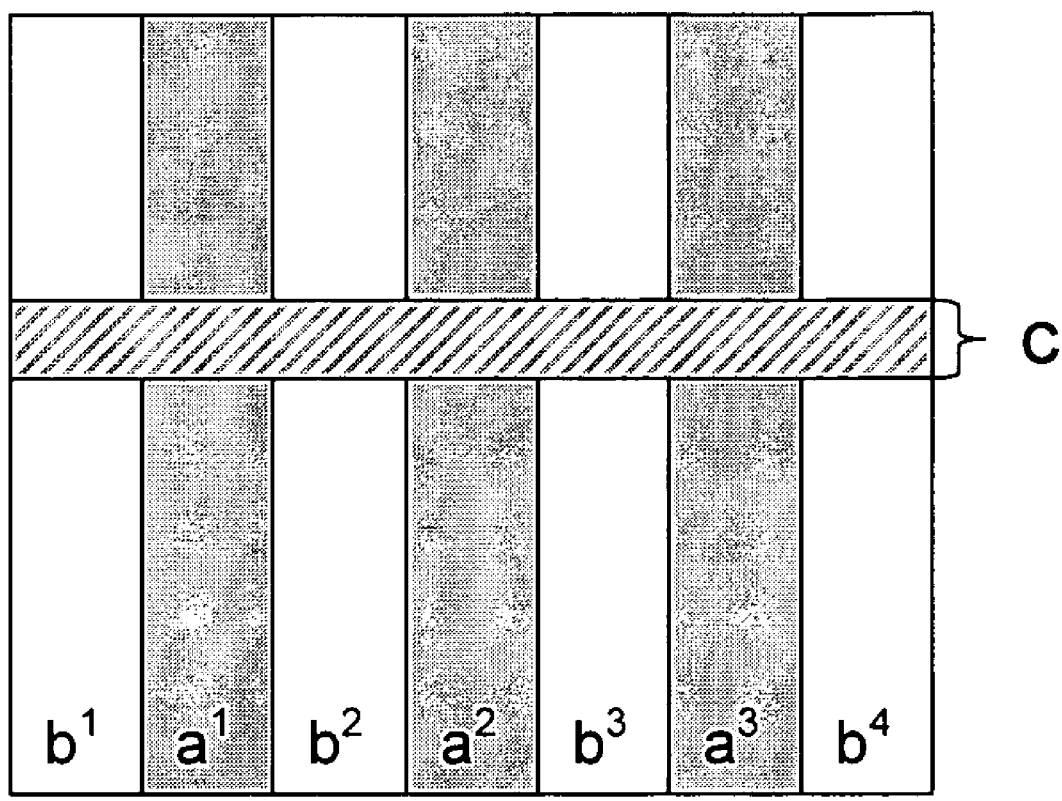
FIG. 3 representatively shows a top plan view of a tissue product comprising the present invention.

When the polysiloxane treatment composition is applied in a non-uniform manner to the fluff pulp fibers, dry lap sheets comprising fluff pulp fibers, webs comprising the fluff pulp fibers, and/or absorbent cores comprising fluff pulp fibers, it is necessary to take the test specimen in a manner so as to replicate the repeat pattern in the web or absorbent core so the sample of the fluff pulp fibers, dry lap sheets comprising fluff pulp fibers, webs comprising the fluff pulp fibers, and/or absorbent cores comprising fluff pulp fibers has the same % area coverage as the rest of the material. For example, referring to FIG. 3, the shaded areas $a^1$, $a^2$, $a^3$ represent polysiloxane treatment composition treated areas on the fluff pulp fibers, dry lap sheets comprising fluff pulp fibers, webs comprising the fluff pulp fibers, and/or absorbent cores comprising fluff pulp fibers (p) while areas $b^1$ through $b^4$ represent untreated areas of the material. In FIG. 3, the polysiloxane treatment composition is applied in stripes in the machine direction. In this test, the test sample strip (C) is taken in the cross direction so that the sample of the fluff pulp fibers, dry lap sheets comprising fluff pulp fibers, webs comprising the fluff pulp fibers, and/or absorbent cores comprising fluff pulp fibers tested has the same ratio of treated to untreated regions as the entire material and hence same proportion of polysiloxane to the polysiloxane treated fluff pulp fibers as the material (p).

As an alternative, the polysiloxane treated fluff pulp fibers, a dry lap sheet comprising the polysiloxane treated fluff pulp fibers, a web comprising the polysiloxane treated fluff pulp fibers, and/or an absorbent core comprising the polysiloxane treated fluff pulp fibers, or a portion thereof may be dry fiberized to obtain a homogeneous distribution of polysiloxane treatment composition in the sample to be tested. Dry fiberization is a dry mechanical treatment in which the material comprising the polysiloxane treated fluff pulp fiber is passed through a device, such as a hammermill, similar to a refiner; the resultant material is polysiloxane treated fluff pulp fiber. Specific equipment and conditions are not important so long as parameters such as anvil gap and feed throughput are controlled so as to achieve good uniformity. This method may be required when using XRF spectroscopy to determine the amount of polysiloxane present in the polysiloxane treated fluff pulp fibers, dry lap sheet comprising the polysiloxane treated fluff pulp fibers, web comprising the polysiloxane treated fluff pulp fibers, or absorbent core comprising the polysiloxane treated fluff pulp fibers. The energy required to conduct the fiberization is reduced by about 25% or greater, more specifically about 30% or greater, more specifically about 35% or greater, and most specifically about 40% or greater at about 4% polysiloxane add-on level.

Representative Fluff Pulp Fibers

A wide variety of natural and synthetic pulp fibers are suitable for use in the dry lap sheets, webs, and/or absorbent cores of the present invention. The fluff pulp fibers may include pulp fibers formed by a variety of pulping processes, such as kraft pulp, sulfite pulp, thermomechanical pulp, etc. In addition, the fluff pulp fibers may consist of any high-average fiber length pulp, low-average fiber length pulp, or mixtures of the same.

One example of suitable high-average length fluff pulp fibers includes softwood kraft pulp fibers. Softwood kraft pulp fibers are derived from coniferous trees and include pulp fibers such as, but not limited to, northern, western, and southern softwood species, including redwood, red cedar, hemlock, Douglas-fir, true firs, pine (e.g., southern pines), spruce (e.g., black spruce), combinations thereof, and the like. Northern softwood kraft pulp fibers may be used in the present invention. One example of commercially available Southern softwood kraft pulp fibers suitable for use in the present invention include those available from Weyerhaeuser Corporation located in Federal Way, Wash. under the trade designation of "NB-416".

Low-average length fibers are often used to increase the softness of the dry lap sheets, webs, and/or absorbent scores of the present invention. An example of suitable low-average length pulp fibers are the so called hardwood kraft pulp fibers. Hardwood kraft pulp fibers are derived from deciduous trees and include pulp fibers such as, but not limited to, eucalyptus, maple, birch, aspen, and the like. In certain instances, eucalyptus kraft pulp fibers may be particularly desired to increase the softness of the dry lap sheet, web and/or absorbent core as well as the disposable absorbent products the polysiloxane treated fluff pulp fibers are incorporated into. Eucalyptus kraft pulp fibers may also enhance the brightness, increase the opacity, and change the pore structure of the tissue sheet to increase its wicking ability.

In disposable absorbent products comprising a blend of hardwood kraft and softwood kraft fibers, the overall ratio of hardwood kraft pulp fibers to softwood kraft pulp fibers within the absorbent core may vary broadly. However, in some embodiments of the present invention, absorbent cores may comprise a blend of hardwood kraft pulp fibers and softwood kraft pulp fibers wherein the ratio of hardwood kraft pulp fibers to softwood kraft pulp fibers is from about 9:1 to about 1:9, more specifically from about 9:1 to about 1:4, and most specifically from about 9:1 to about 1:3. In one embodiment of the present invention, the hardwood kraft pulp fibers and softwood kraft pulp fibers (polysiloxane pretreated pulp fibers and/or non-treated pulp fibers) may be layered so as to give a heterogeneous distribution of hardwood kraft pulp fibers and softwood kraft pulp fibers in the z-direction of the absorbent core. In another embodiment, the hardwood and softwood fibers may be combined in a blended sheet wherein the hardwood kraft fibers and softwood kraft fibers are distributed homogeneously in the z-direction.

In addition, other pulping processes may be used to produce suitable hardwood or softwood fluff pulp fibers for disposable absorbent products, and are suitable as an embodiment of the present invention. Examples of pulping processes include, but are not limited to, acid-sulfite, bisulfite, neutral sulfite, soda process, mechanical pulping, and chemi-mechanical pulping, and chemi-thermal mechanical pulping. Additionally, the fibers may be unbleached, partially bleached, or fully bleached.

In addition, synthetic fibers may also be utilized. The discussion herein regarding pulp fibers is understood to include synthetic fibers. Some suitable polymers that may be used to form the synthetic fibers include, but are not limited to: polyolefins, such as, polyethylene, polypropylene, polybutylene, and the like; polyesters, such as polyethylene terephthalate, poly(glycolic acid) (PGA), poly(lactic acid) (PLA), poly(β-malic acid) (PMLA), poly(ε-caprolactone) (PCL), poly(ρ-dioxanone) (PDS), poly(3-hydroxybutyrate) (PHB), and the like; and, polyamides, such as nylon and the like. Synthetic or natural cellulosic polymers, including but not limited to: cellulosic esters; cellulosic ethers; cellulosic nitrates; cellulosic acetates; cellulosic acetate butyrates; ethyl cellulose; regenerated celluloses, such as viscose, rayon, and the like. Non-wood fibers may also be used, including fiber originating from hemp, straw, flax, bagasse, and mixtures thereof may be used in the present invention. The synthetic or non-wood fibers may be located throughout the absorbent core or in any or all layers of the absorbent core.

Another aspect the present invention resides in a method for making a polysiloxane treated fluff pulp fiber having a high level of polydialkylsiloxane and demonstrating the desired level of flexibility, yet having desired wettability.

In a specific embodiment of the present invention, at least a portion of the polysiloxane is delivered to the absorbent core of the disposable absorbent product via polysiloxane treated fluff pulp fibers. The preparation of polysiloxane treated fluff pulp fibers may be accomplished by methods such as those described in U.S. Pat. No. 6,582,560 issued to Runge, et. al., on Jun. 24, 2003, the disclosure of which is incorporated herein by reference to the extent that it is non-contradictory herewith. It has been found that fluff pulp fibers treated with polysiloxane in this manner demonstrate excellent retention of the polysiloxane through the tissue making process. The polysiloxane treated fluff pulp fibers may contain from about 0.1% to about 10% polysiloxane by weight, more specifically from about 0.2% to about 4% polysiloxane by weight, and most specifically from about 0.3% polysiloxane to about 3% polysiloxane by weight. The polysiloxane treated fluff pulp fibers may be blended with non-treated polysiloxane fluff pulp fibers in the absorbent cores of the disposable absorbent products.

The amount of treated fluff pulp fiber incorporated into the absorbent core of an absorbent product may range from about 5% to about 100% and is not overly critical provided the specific product requirements of the present invention are met.

Other Chemical Additives

Optional chemical additives may also be applied to the fluff pulp fiber of the present invention, to either aqueous slurries of the fluff pulp fibers, dried fluff pulp fibers, sheets of fluff pulp fibers, and/or to the absorbent core, to impart additional benefits to the fluff pulp fibers and/or the disposable absorbent product and are not antagonistic to the intended benefits of the present invention. The following chemical additives are examples of additional chemical treatments that may be applied to the fluff pulp fibers and/or the absorbent cores of the disposable absorbent products comprising the polysiloxane treated fluff pulp fibers. The chemical additives are included as examples and are not intended to limit the scope of the present invention. Such chemical additives may be added at any point in the treatment process of the fluff pulp fibers and/or the manufacture of the absorbent core of a disposable absorbent product. The chemical additives may also be added in conjunction with the polysiloxane treatment composition during the treatment process.

It is also understood that the optional chemical additives may be employed in specific layers of the fluff pulp fibers and/or absorbent core or may be employed throughout the fluff pulp fibers and/or absorbent core as broadly known in the art. One such class of additive are binders to assist densification of particle containment. Suitable materials are described, but not limited to, in U.S. Pat. No. 2,757,150 issued to Heritage on Jul. 31, 1956; U.S. Pat. No. 4,584,357 issued to Harding et al. on Apr. 22, 1986; U.S. Pat. No. 4,600,462 issued to Watt on Jul. 15, 1986; and, U.S. Pat. No. 5,547,541 issued to Hansen et al. on Aug. 20, 1996. Other chemical additives include crosslinking agents that form covalent intrafiber bonds to change fiber absorbent properties. Suitable materials are described, but not limited to, in U.S. Pat. No. 3,224,926 issued to Bernarden on Dec. 21, 1965; U.S. Pat. No. 3,440,135 issued to Chung on Apr. 22, 1969; U.S. Pat. No. 3,241,553 issued to Steiger on Mar. 22, 1969; and, U.S. Pat. No. 4,898,642 issued to Moore et al. on Feb. 6, 1990. Other chemical treatments that may also be used with the present invention would treatments to improve fiberization. Suitable materials are described in, but not limited to, U.S. Pat. No. 4,432,833 issued to Breese on Feb. 21, 1984; U.S. Pat. No. 4,425,186 issued to May et al. on Jan. 10, 1984; U.S. Pat. No. 4,303,471 issued to Laursen on Dec. 1, 1981; U.S. Pat. No. 4,469,746 issued to Weisman et al. on Sep. 4, 1984; U.S. Pat. No. 5,068,009 issued to Jokinen et al. on Nov. 26, 1991; U.S. Pat. No. 5,489,469 issued to Koboyashi et al. on Feb. 6, 1996; and, U.S. Pat. No. 5,492,759 issued to Eriksson et al. on Feb. 20, 1996.

Representative Disposable Absorbent Product

The disposable absorbent products of the present invention will be described in terms of a disposable diaper article. It is understood that the features of the present invention are equally adaptable for other types of disposable absorbent products such as adult incontinence pads, adult incontinence garments, training pants, disposable swim pants and feminine hygiene pads.

Figure 2:
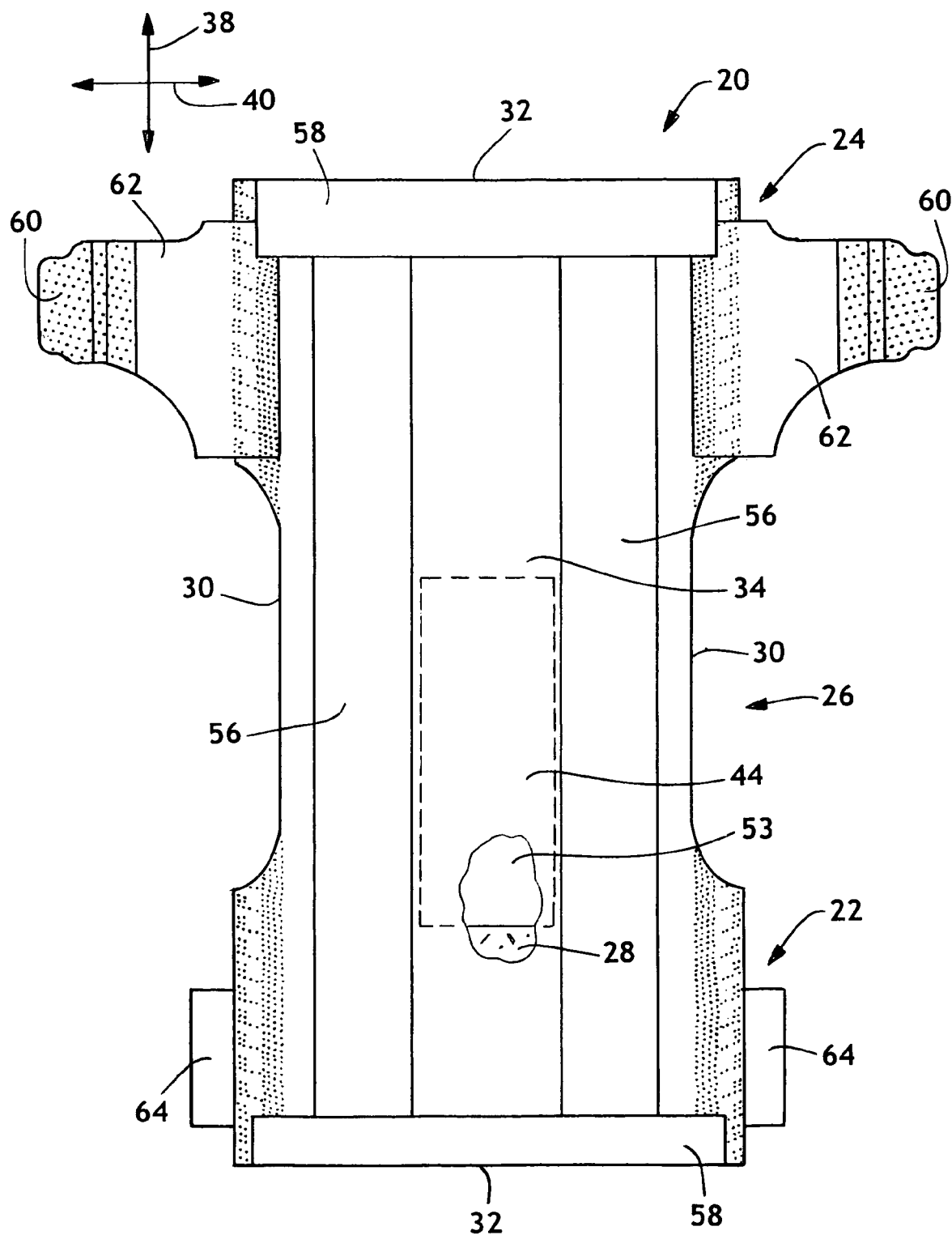
FIG. 2 representatively shows a plan view of the disposable absorbent article of FIG. 1 in an unfastened, stretched and laid flat condition with the surface of the article which contacts the wearer's skin facing the viewer and with portions of the article partially cut away to show the underlying features.

FIG. 1 representatively illustrates an example of a refastenable disposable diaper, as generally indicated at 20, of the present invention. FIG. 2 representatively illustrates the refastenable disposable diaper of FIG. 1 in an unfastened, stretched and laid flat configuration with the surface of the disposable diaper 20 adapted to contact the wearer's skin facing the viewer and with portions of the disposable diaper 20 partially cut away to show the underlying features. As illustrated in FIG. 2, the disposable diaper 20 defines a front waist region 22, a back waist region 24, a crotch region 26 that extends between and connects the front and back waist regions 22 and 24, respectively, a longitudinal direction 38 and a lateral direction 40. The front waist region 22 includes the portion of the disposable diaper 20 that, when worn, is positioned on the front of the wearer while the back waist region 24 includes the portion of the disposable diaper 20 that, when worn, is positioned on the back of the wearer. The crotch region 26 of the disposable diaper 20 includes the portion of the disposable diaper 20 that, when worn, is positioned between the legs of the wearer and covers the lower torso of the wearer.

The disposable diaper 20 defines a pair of laterally opposed side edges 30, a pair of longitudinally opposed waist edges 32, an interior surface 34 that is configured to contact the wearer, and an exterior surface 36 opposite the interior surface 34 that is configured to contact the wearer's clothing in use. The illustrated disposable diaper 20 also includes a substantially liquid impermeable outer cover 42 and a liquid permeable bodyside liner 44 that can be connected to the outer cover 42 in a superposed relation. An absorbent core 28 is located between the outer cover 42 and the bodyside liner 44. The laterally opposed side edges 30 of the disposable diaper 20 are generally defined by the side edges of the outer cover 42 that further define leg openings that may be curvilinear. The waist edges 32 of the disposable diaper 20 are generally defined by the waist edges 32 of the outer cover 42 and define a waist opening that is configured to encircle the waist of the wearer when worn. The absorbent core 28 is configured to contain and/or absorb body exudates discharged from the wearer. The disposable diaper 20 may further include leg elastics 54, containment flaps 56 and waist elastics 58 as are known to those skilled in the art. It should be recognized that individual components of the disposable diaper 20 may be optional depending upon the intended use of the disposable diaper 20.

The disposable diaper 20 may further include refastenable mechanical fasteners 60. The mechanical fasteners 60 releasably engage the opposed side edges 30 of the disposable diaper 20 in the front and back waist regions 22 and 24, respectively. The mechanical fasteners 60 may include a variety of materials and surfaces known for 20 mechanical engagement, including, but not limited to buttons, pins, snaps, adhesive tape fasteners, cohesives, mushroom-and-loop fasteners, and hook and loop fasteners. Further, the disposable diaper 20 may include an attachment panel 66 located on the front or back waist region 22 and 24, opposite the mechanical fasteners 60 to which the mechanical fasteners 60 may be releasably engaged during use of the disposable diaper 20.

The disposable diaper 20 may be of various suitable shapes. For example, in the unfastened configuration of the disposable diaper 20 as illustrated in FIG. 2, the disposable diaper 20 may have an overall rectangular shape, T-shape or an approximately hourglass shape. In the shown embodiments, the disposable diaper 20 has a generally I-shape in an unfastened configuration.

The various components of the disposable diaper 20 are integrally assembled together employing various types of suitable attachment means, such as adhesive, sonic and thermal bonds or combinations thereof. In the shown embodiments, for example, the outer cover 42 and bodyside liner 44 are assembled to each other and to the absorbent core 28 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Alternatively, the absorbent core 28 may be connected to the outer cover 42 using conventional fasteners such as buttons, hook and loop type fasteners, adhesive tape fasteners, and the like. The other components of the disposable diaper 20 may be suitably connected together using similar means. Similarly, other diaper components, such as the elastic members 54 and 58 and the mechanical fasteners 60, may be assembled into the disposable diaper 20 by employing the above-identified attachment mechanisms. In the alternative, the majority of the components of the disposable diaper 20 may be assembled together using ultrasonic bonding techniques for reduced manufacturing cost.

The outer cover 42 of the disposable diaper 20, as representatively illustrated in FIG. 1, may suitably be composed of a material which is either liquid permeable or liquid impermeable. It is generally preferred that the outer cover 42 be formed from a material that is substantially impermeable to liquids. A typical outer cover 42 may be manufactured from a thin plastic film or other flexible liquid-impermeable material. For example, the outer cover 42 may be formed from a polyethylene film having a thickness of from about 0.013 millimeter (0.5 mil) to about 0.051 millimeter (2.0 mils). The materials of the outer cover 42 may be thermally or adhesively laminated together. Suitable laminate adhesives, which may be applied continuously or intermittently as beads, a spray, parallel swirls, or the like, can be obtained from Bostik-Findley, Inc., of Wauwatosa, Wis., U.S.A., or from National Starch and Chemical Company, Bridgewater, N.J., U.S.A. If it is desired to present the outer cover 42 with a more clothlike feeling, the outer cover 42 may be formed from a polyolefin film having a nonwoven web laminated to the exterior surface thereof, such as a spunbond web of polyolefin fibers. For example, a stretch-thinned polypropylene film having a thickness of about 0.015 millimeter (0.6 mil) may be thermally laminated thereto a spunbond web of polypropylene fibers. The polypropylene fibers may have a fiber diameter of about 15 to 20 microns, which nonwoven web has a basis weight of about 17 grams per square meter (0.5 ounce per square yard). The outer cover 42 may include bicomponent fibers such as polyethylene/polypropylene bicomponent fibers. Methods of forming such clothlike outer covers are known to those skilled in the art. The outer cover 42 may also be an extensible outer cover such as the outer covers described in U.S. Pat. No. 6,552,245 issued on Apr. 22, 2003 to Roessler et al. The outer cover 42 may also be a biaxially stretchable outer cover such as the outer covers described in U.S. patent application Ser. No. 09/698,517 filed on Oct. 27, 2000 by Vukos et al.

The outer cover 42 may be formed of a woven or nonwoven fibrous web layer which has been totally or partially constructed or treated to impart a desired level of liquid impermeability to selected regions that are adjacent or proximate the absorbent core 28. Still further, the outer cover 42 may optionally be composed of a micro-porous "breathable" material which permits vapors to escape from the absorbent core 28 while still preventing liquid exudates from passing through the outer cover 42. For example, the outer cover 42 may include a vapor permeable non-woven facing layer laminated to a micro-porous film. Suitable "breathable" outer cover materials are described in U.S. Pat. No. 5,695,868 issued on Dec. 9, 1997 to McCormack et al. and U.S. Pat. No. 5,843,056 issued on Dec. 1, 1998 to Good et al., the descriptions of which are hereby incorporated by reference. Still further, the outer cover 42 may also be an elastomeric material such as a stretch-thermal laminate (STL), neck-bonded laminate (NBL), or stretch-bonded laminate (SBL) material. Methods of making such materials are well known to those skilled in the art and are described in U.S. Pat. No. 4,663,220 issued on May 5, 1987 to Wisneski et al.; U.S. Pat. No. 5,226,992 issued on Jul. 13, 1993 to Morman; and, European Patent Application No. EP 0 217 032 published on Apr. 8, 1987 in the names of Taylor et al., the disclosures of which are incorporated herein by reference to the extent that they are non-contradictory herewith. The outer cover 42 may also be embossed or otherwise provided with a matte finish to provide a more aesthetically pleasing appearance.

In order to reduce the perception that the outer cover 42 feels damp or clammy, the disposable diapers 20 of the present invention may include a spacer or ventilation layer (not shown in Figures) between the garment-facing surface of the absorbent core 28 and the outer cover 42. The ventilation layer may include one or more nonwoven materials, for example a spunbond-meltblown-spunbond nonwoven material.

The representative disposable absorbent products of the present invention include a bodyside liner 44 in superimposed relation to the outer cover 42. The bodyside liner 44, as representatively illustrated in FIG. 2, suitably presents a bodyfacing surface that is compliant, soft feeling, and nonirritating to the wearer's skin. Further, the bodyside liner 44 may be less hydrophilic than the absorbent core 28, to present a relatively dry surface to the wearer, and may be sufficiently porous to be liquid permeable, permitting liquid to readily penetrate through its thickness. A suitable bodyside liner 44 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 44 is suitably employed to help isolate the wearer's skin from liquids held in the absorbent core 28. The bodyside liner 44 may also be made from extensible materials as are described in U.S. Pat. No. 6,552,245 issued on Apr. 22, 2003 to Roessler et al. The bodyside liner 44 may also be made from biaxially stretchable materials as are described in U.S. patent application Ser. No. 09/698,517 filed on Oct. 27, 2000 by Vukos et al.

Various woven and nonwoven fabrics can be used for the bodyside liner 44. For example, the bodyside liner 44 may be composed of a meltblown or spunbond web of polyolefin fibers. The bodyside liner 44 may also be a bonded-carded web composed of natural and/or synthetic fibers. The bodyside liner 44 may be composed of a substantially hydrophobic material, and the hydrophobic material may optionally be treated with a surfactant or otherwise processed to impart a desired level of wettability and hydrophilicity. In a particular embodiment of the present invention, the bodyside liner 44 is made from a nonwoven, spunbond, polypropylene fabric composed of fibers having a fiber diameter of about 21 to 23 microns formed into a web having a basis weight of about 20 grams per square meter and a density of about 0.13 grams per cubic centimeter. The fabric may be surface treated with about 0.3 weight percent of a surfactant, such as a surfactant commercially available from Hodgson Textile Chemicals, Inc. under the trade designation AHCOVEL Base N-62. The surfactant may be applied by any conventional means, such as spraying, printing, brush coating or similar techniques. The surfactant may be applied to the entire bodyside liner 44 or may be selectively applied to particular sections of the bodyside liner 44, such as the medial section along the longitudinal centerline of the diaper, to provide greater wettability of such sections. The bodyside liner 44 may further include a lotion or treatment applied thereto that is configured to be transferred to the wearer's skin. Suitable compositions for application to the bodyside liner 44 are described in U.S. Pat. No. 6,149,934 that issued to Krzysik et al. on Nov. 21, 2000.

The representative disposable absorbent products of the present invention may include an absorbent core 28 disposed between the outer cover 42 and the bodyside liner 44. The absorbent core 28 of the disposable diaper 20, as representatively illustrated in FIG. 2, may suitably include a matrix of hydrophilic fluff pulp fibers, such as a web of cellulosic fluff, mixed with particles of a high-absorbency material commonly known as superabsorbent material. In a particular aspect, the absorbent core 28 includes a matrix of cellulosic fluff, such as wood pulp fluff, and superabsorbent hydrogel-forming particles. The wood fluff pulp fluff may be exchanged with synthetic, polymeric, meltblown fibers or with a combination of meltblown fibers and natural fibers. The superabsorbent particles may be substantially homogeneously mixed with the hydrophilic fluff pulp fibers or may be nonuniformly mixed. Alternatively, the absorbent core 28 may include a laminate of fibrous webs and superabsorbent material or other suitable matrix for maintaining a superabsorbent material in a localized area.

The absorbent core 28 may have any of a number of shapes. For example, the absorbent core 28 may be rectangular, I-shaped, or T-shaped. It is generally preferred that the absorbent core 28 is narrower in the intermediate section than in the front or back waist sections 22 and 24, respectively, of the disposable diaper 20. The absorbent core 28 may be provided by a single layer or, in the alternative, may be provided by multiple layers, all of which need not extend the entire length and width of the absorbent core 28. In a particular aspect of the present invention, the absorbent core 28 may be generally T-shaped with the laterally extending cross-bar of the "T" generally corresponding to the front waist region 22 of the disposable diaper 20 for improved performance, especially for male infants.

The size and the absorbent capacity of absorbent core 28 should be compatible with the size of the intended wearer and the liquid loading imparted by the intended use of the absorbent product. Further, the size and the absorbent capacity of the absorbent core 28 may be varied to accommodate wearers ranging from infants through adults. In addition, it has been found that with the present invention, the densities and/or basis weights of the absorbent core 28 may be varied. In some embodiments, the basis weight of the absorbent core 28 may range from about 50 $g/m^2$ to about 1000 $g/m^2$. In other embodiments, the basis weight of the absorbent core 28 may range from about 100 $g/m^2$ to about 800 $g/m^2$. In still other embodiments, the basis weight of the absorbent core 28 may range from about 150 $g/m^2$ to about 600 $g/m^2$. The basis weight of the absorbent core 28 may be about 50 $g/m^2$ or greater, more specifically about 100 $g/m^2$ or greater, or more specifically about 150 $g/m^2$ or greater. In some embodiments, the density of the absorbent core 28 may range from about 0.05 $g/cm^3$ to about 0.8 $g/cm^3$. In other embodiments, the density of the absorbent core 28 may range from about 0.1 $g/cm^3$ to about 0.6 $g/cm^3$. In still other embodiments, the density of the absorbent core 28 may range from about 0.2 $g/cm^3$ to about 0.4 $g/cm^3$. The density of the absorbent core 28 may be about 0.05 $g/cm^3$ or greater, more specifically about 0.1 $g/cm^3$ or greater, or more specifically about 0.2 $g/cm^3$ or greater.

The superabsorbent material may be selected from natural, synthetic, and modified natural polymers and materials. The superabsorbent materials may be inorganic materials, such as silica gels, or organic compounds, such as crosslinked polymers. The term "crosslinked" refers to methods for effectively rendering normally water-soluble materials substantially water insoluble but swellable. Such methods include, for example, physical entanglement, crystalline domains, covalent bonds, ionic complexes and associations, hydrophilic associations such as hydrogen bonding, and hydrophobic associations or Van der Waals forces.

Examples of synthetic, polymeric, superabsorbent materials include the alkali metal and ammonium salts of poly (acrylic acid) and poly(methacrylic acid), poly(acrylamides), poly(vinyl ethers), maleic anhydride copolymers with vinyl ethers and alpha-olefins, poly(vinyl pyrrolidone), poly(vinyl morpholinone), poly(vinyl alcohol), and mixtures and copolymers thereof. Further polymers suitable for use in the absorbent core 28 include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum, and the like. Mixtures of natural and wholly or partially synthetic absorbent polymers may also be useful in the present invention.

The superabsorbent material may be in any of a wide variety of geometric forms. As a general rule, typically the superabsorbent material may be in the form of discrete particles. However, the superabsorbent material may also be in the form of fibers, flakes, rods, spheres, needles, or the like. In general, the superabsorbent material is present in the absorbent core 28 in an amount of from about 5 to about 90 percent by weight, desirably in an amount of at least about 30 percent by weight, and even more desirably in an amount of at least about 50 percent by weight based on a total weight of the absorbent core 28. For example, in a particular aspect, the absorbent core 28 may include a laminate which includes at least about 50 percent by weight and desirably at least about 70 percent by weight of superabsorbent material overwrapped by a fibrous web or other suitable material for maintaining the superabsorbent material in a localized area.

An example of superabsorbent material suitable for use in the present invention is DRYTECH 2035 polymer available from Dow Chemical, a business having offices in Midland, Mich. Other suitable superabsorbent materials may include FAVOR SXM 880 polymer obtained from Stockhausen, a business having offices in Greensboro, N.C.

Optionally, a substantially hydrophilic tissue or nonwoven wrapsheet (not illustrated) may be employed to help maintain the integrity of the structure of the absorbent core 28. The wrapsheet is typically placed about the absorbent core 28. The wrapsheet may be composed of an absorbent cellulosic material, such as creped wadding or a high wet-strength tissue. In one aspect of the present invention, the wrapsheet may be configured to provide a wicking layer that helps to rapidly distribute liquid over the mass of fluff pulp fibers and/or superabsorbent materials constituting the absorbent core 28.

Due to the thinness of absorbent core 28 and the superabsorbent material, such as the superabsorbent materials, within the absorbent core 28, the liquid uptake rates of the absorbent core 28, by itself, may be too low, or may not be adequately sustained over multiple insults of liquid into the absorbent core 28. To improve the overall liquid uptake and air exchange, the disposable diaper 20 of the different aspects of the present invention may further include a porous, liquid-permeable layer of surge management material 53, as representatively illustrated in FIG. 2. The surge management layer 53 is typically less hydrophilic than the absorbent core 28, and has an operable level of density and basis weight to quickly collect and temporarily hold liquid surges, to transport the liquid from its initial entrance point and to substantially completely release the liquid to other parts of the absorbent core 28. This configuration can help prevent the liquid from pooling and collecting on the portion of the disposable diaper 20 positioned against the wearer's skin, thereby reducing the feeling of wetness by the wearer. The structure of the surge management layer 53 also generally enhances the air exchange within the disposable diaper 20.

Various woven and nonwoven fabrics may be used to construct the surge management layer 53. For example, the surge management layer 53 may be a layer composed of a meltblown or spunbond web of synthetic fibers, such as polyolefin fibers. The surge management layer 53 may also be a bonded-carded-web or an airlaid web composed of natural and synthetic fibers. The bonded-carded-web may, for example, be a thermally bonded web that is bonded using low melt binder fibers, powder or adhesive. The webs can optionally include a mixture of different fibers. The surge management layer 53 may be composed of a substantially hydrophobic material, and the hydrophobic material may optionally be treated with a surfactant or otherwise processed to impart a desired level of wettability and hydrophilicity. In a particular aspect, the surge management layer 53 includes a hydrophobic, nonwoven material having a basis weight of from about 30 to about 120 grams per square meter.

The absorbent products of the present invention may also include additional components. For example, as representatively illustrated in FIGS. 1 and 2, the disposable diaper 20 may include a pair of containment flaps 56 that are configured to provide a barrier to the lateral flow of body exudates. The containment flaps 56 may be located along the laterally opposed side edges 30 of the disposable diaper 20 adjacent the side edges of the absorbent core 28. Each containment flap 56 typically defines an unattached edge that is configured to maintain an upright, perpendicular configuration in at least the crotch region 26 of the disposable diaper 20 to form a seal against the wearer's body. The containment flaps 56 may extend longitudinally along the entire length of the absorbent core 28 or may only extend partially along the length of the absorbent core 28. When the containment flaps 56 are shorter in length than the absorbent core 28, the containment flaps 56 may be selectively positioned anywhere along the side edges 30 of disposable diaper 20 in the crotch region 26. In a particular aspect of the present invention, the containment flaps 56 extend along the entire length of the absorbent core 28 to better contain the body exudates. Such containment flaps 56 are generally well known to those skilled in the art.

The disposable diaper 20 of the different configurations of the present invention may further include elastics at the waist edges 32 and side edges 30 of the disposable diaper 20 to further prevent leakage of body exudates and support the absorbent core 28. For example, as representatively illustrated in FIGS. 1 and 2, the disposable diaper 20 of the present invention may include a pair of leg elastic members 54 that are connected to the laterally opposed side edges 30 of the disposable diaper 20 in the crotch region 26. The disposable diaper 20 may also include a pair of waist elastic members 58 that are connected to the longitudinally opposed waist edges 32 of the disposable diaper 20. The leg elastics 54 and waist elastics 58 are generally adapted to fit about the legs and waist, respectively, of a wearer in use to maintain a positive, contacting relationship with the wearer to effectively reduce or eliminate the leakage of body exudates from the disposable diaper 20.

Materials suitable for use as the leg elastics 54 and waist elastics 58 are well known to those skilled in the art. Exemplary of such materials are sheets or strands or ribbons of a polymeric, elastomeric material that may be adhered to the outer cover 42 in a stretched position, or that may be attached to the outer cover 42 while the outer cover is pleated, such that elastic constrictive forces are imparted to the outer cover 42. The leg elastics 54 may also include such materials as polyurethane, synthetic and natural rubber. The waist elastics 58 may be formed by elastic strands attached to the outer cover 42 or they may be formed by attaching separate pieces of stretchable materials to the waist regions of the absorbent product. For example, the waist elastics 58 may include a piece of stretch-bonded laminate material attached to the interior surface 34 of the absorbent product to form a waistband. Elasticity may be added or incorporated into the waist opening of absorbent products utilizing a variety of known approaches.

The disposable absorbent products of the present invention may include one or more components that extend laterally outward from the longitudinal sides of the absorbent product. Typically, the longitudinal sides are defined by the materials forming the chassis of the disposable diaper 20. The chassis may be defined by the outer cover 42 and bodyside liner 44 materials. Components that extend laterally outward may include front ear portions 64 and back ear portions 62. The front ear portions 64 and the back ear portions 62 may be formed of one or more materials and may include laminates of materials. The front ear portions 64 and the back ear portions 62 improve the fit of the absorbent article. More specifically, the front ear portions 64 may provide additional coverage around the waist of the wearer and they may assist caregivers with positioning the front waist region 22 on the wearer of the article. The front ear portions 64 may also include mechanical fastening materials such that the front ear portions 64 contribute to the overall fastening system of the article. The back ear portions 62 may also provide coverage around the waist of the wearer. More specifically, the back ear portions 62 may provide the bridging material between the back waist region 24 of the article and the front waist region 22 such that the back ear portions 62 form part of the article's waist opening and an upper edge of the article's leg openings. Additionally, the back ear portions 62 may include fastening materials that facilitate joining of the back waist region 24 with the front waist region 22. For example, the back ear portions 62 may include mechanical fasteners 60 selected for engagement with an attachment panel 66 in the front waist region 22 of the article.

Presently available infant diapers typically include back ear portions 62 that include a stretchable material. When the back ear portions 62 include a stretchable material, the back ear portions 62 may increase the range with which the mechanical fasteners 60 may be engaged into the attachment panel 66 or directly into the outer cover 42. Further, when the back ear portions 62 include a stretchable material, the article may be worn by a greater range of users as a result of the increased fit range. An exemplary material from which the back ear portions 62 may be constructed is a necked bonded laminate material having two nonwoven (e.g. spunbond) facings with an elastomeric film (e.g. KRATON film) laminated in between. Other suitable stretchable materials are known in the art. Depending on the design of the disposable diaper 20, it may also be desirable for the front ear portions 64 to include a stretchable material.

Analytical Methods

Liquid Saturation Retention Capacity Test

Figure 4:
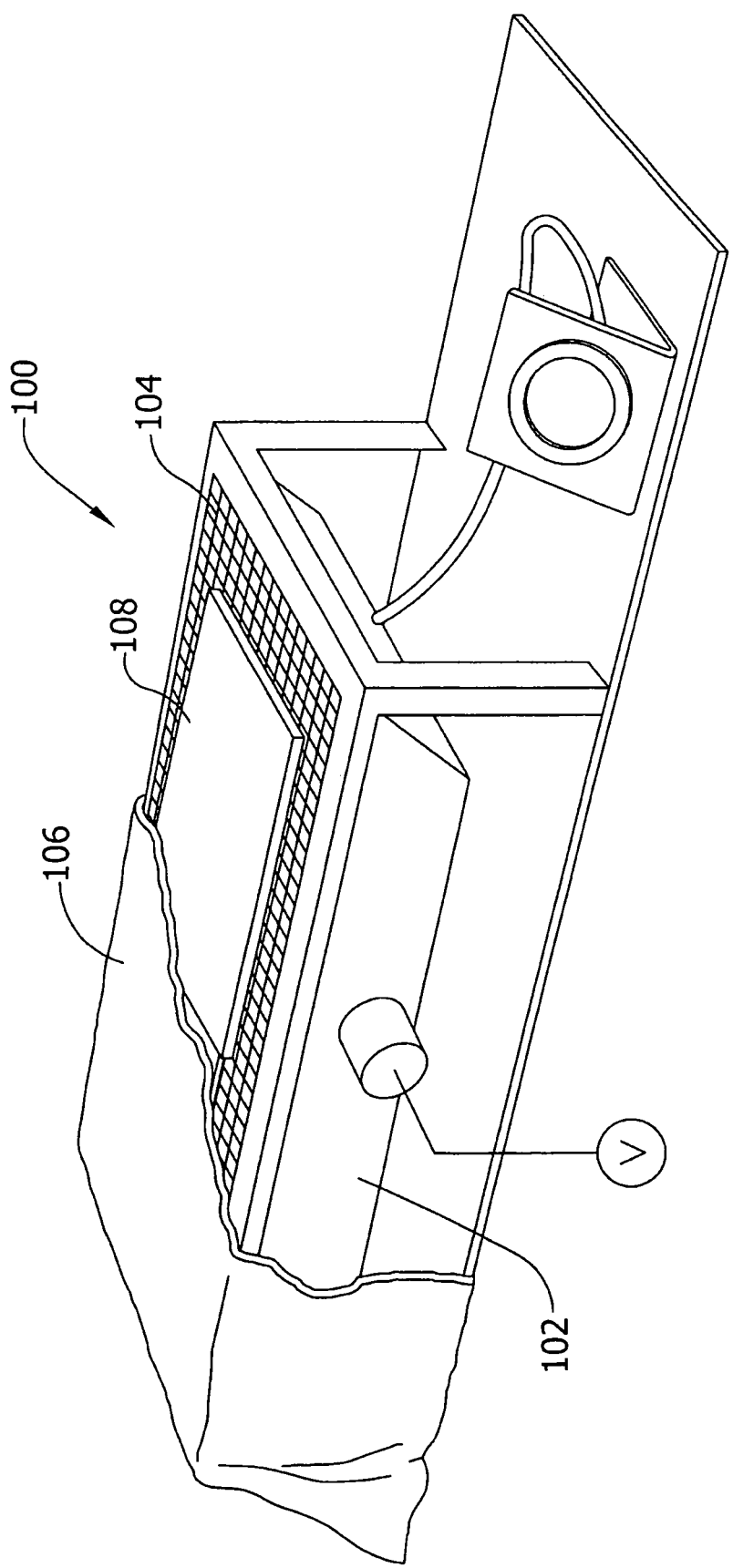
FIG. 4 representatively shows a cross-section of an apparatus for conducting a Liquid Retention Capacity Test.

The following test is used to determine a retention capacity of an absorbent structure, i.e., the capacity of the absorbent structure for retaining liquid therein. A circular absorbent structure sample 108 having a diameter of 3 inches (approximately 7.6 cm) is weighed with the tissue wrap material on and the weight in grams is recorded. The absorbent structure sample 108 may also be square in shape. The absorbent structure sample 108 is then wrapped in toweling (not shown), such as Scott Hi-Dri available from Kimberly-Clark of Neenah, Wis., U.S.A., and submerged in an excess quantity of test solution (i.e., 0.9 weight percent saline solution at about 23 degrees Celsius) for twenty minutes. After this time period, the absorbent structure sample 108 is removed from the test solution and placed on a retention capacity test apparatus, indicated generally at 100 in FIG. 4, comprising a vacuum box 102, a TEFLON fiberglass screen 104 having 0.25 inch (0.6 cm) openings and supported by the vacuum box 102, and a flexible rubber cover 106 sized for overlaying the screen 104 on the vacuum box 102.

More particularly, the absorbent structure sample 108 (with toweling) is placed uncovered (e.g., by the rubber cover 106) on the screen 104 and allowed to drip dry for about one minute. The rubber cover 106 is then placed over the absorbent structure sample 108 and screen 104 (e.g., to generally form a seal over the vacuum box 102) and a vacuum (V) of about 0.5 MPa (about 34.5 dynes/square cm) is drawn on the vacuum box 102 (and hence the absorbent structure sample 108) for a period of about five minutes. The absorbent structure sample 108 is then removed from the toweling, making an effort to recover loose fibers and superabsorbent particles along with the absorbent structure sample 108. The recovered absorbent structure sample 108 is again weighed and the weight in grams is recorded. A "total retention capacity" of the absorbent structure sample 108 is determined by subtracting the dry weight of the absorbent structure sample 108 from the weight of the recovered absorbent structure sample 108 after application of the vacuum and is recorded as grams of liquid retained. For relative comparisons to absorbent structures of different mass, a "normalized retention capacity" is determined as the total retention capacity divided by the dry weight of the absorbent structure sample 108 and is recorded as grams of liquid retained per gram of absorbent structure (g/g, or $g_{liq.}/g_{abs.}$).

If the fluff pulp fibers and/or superabsorbent material of the absorbent structure sample 108 are drawn through the fiberglass screen 104 into the vacuum box 102 during testing, a screen having smaller openings should be used and the test should be re-done. Alternatively, a piece of tea bag material or other similar material can be placed between the absorbent structure sample 108 and the screen 104 and the total retention capacity adjusted for the liquid retained by the tea bag or other material.

At least three samples of each absorbent structure are tested and the results are averaged to provide the retention capacity (e.g., total and normalized retention capacity) of the absorbent structure.

Fluid Intake Flowback Evaluation Test

Figure 5:
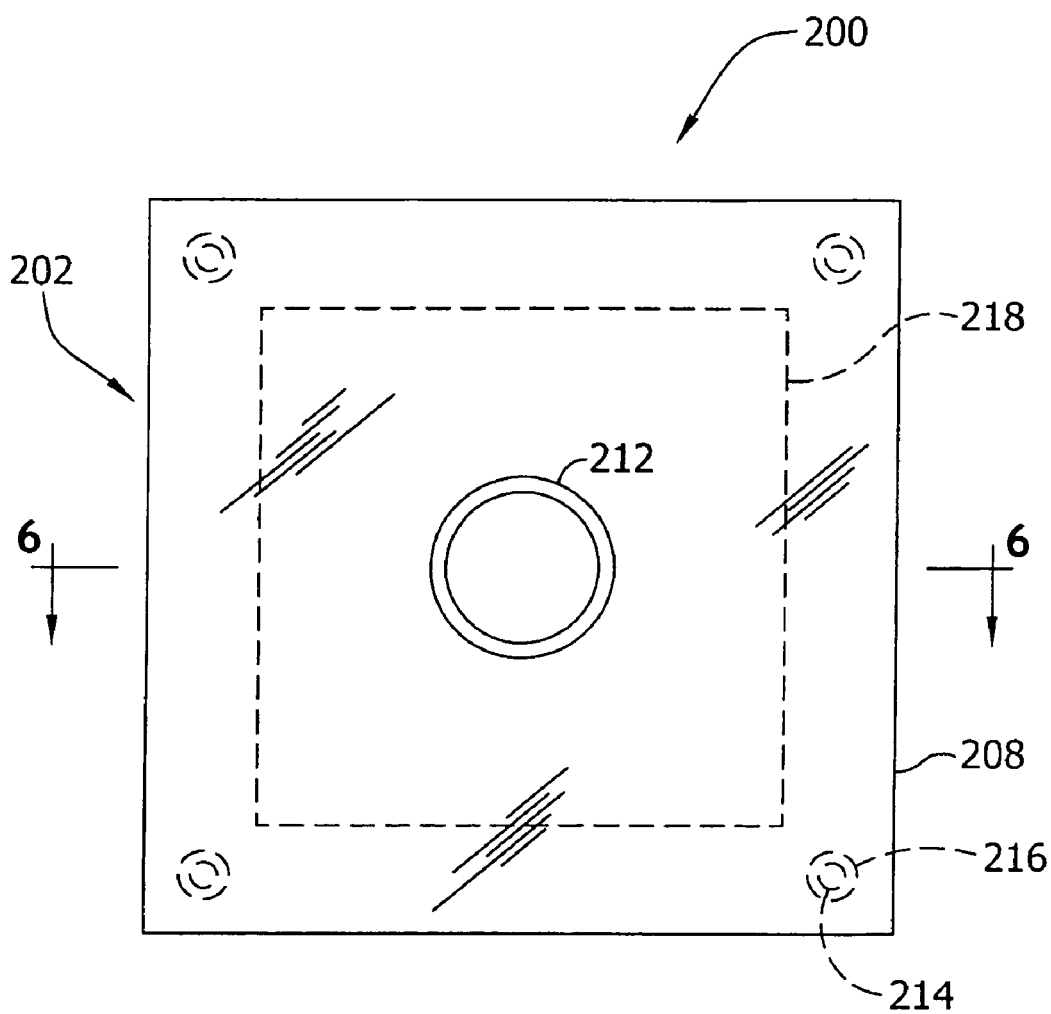
FIG. 5 representatively shows a top plan view of an apparatus for conducting a Fluid Intake Evaluation Test.
Figure 6:
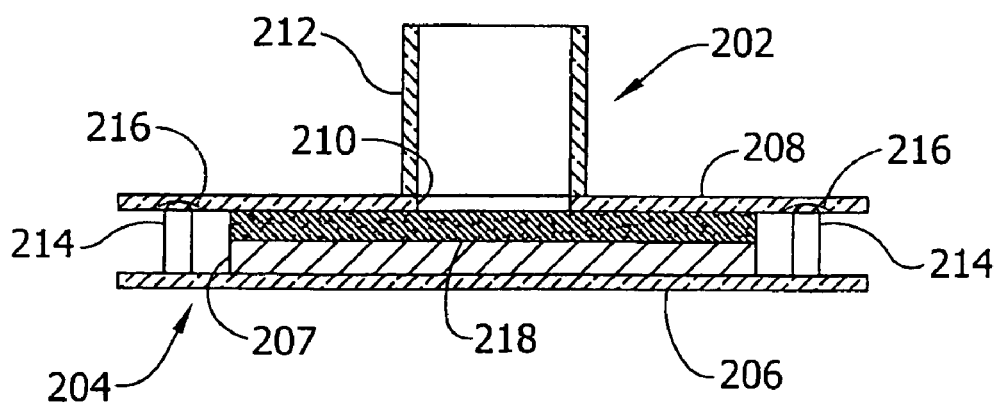
FIG. 6 representatively shows a section taken in the plane of line 6-6 of FIG. 5.

The Fluid Intake Flowback Evaluation (FIFE) Test determines the amount of time required for an absorbent structure, and more particularly a sample thereof, to take in (but not necessarily absorb) a known amount of test solution (0.9 weight percent saline solution). A suitable apparatus for performing the FIFE Test is shown in FIGS. 5 and 6 and is generally indicated at 200. The test apparatus 200 comprises upper and lower assemblies, generally indicated at 202 and 204, respectively. The lower assembly 204 comprises a generally 7 inch by 7 inch (45 cm by 45 cm) square lower plate 206 constructed of a transparent material such as plexiglass and a generally 4.5 inch (11.4 cm) by 4.5 inch (11.4 cm) square platform 207 centered on the lower plate 206 for centering the absorbent structure sample 218 during the test.

The upper assembly 202 comprises a generally square upper plate 208 constructed similar to the lower plate 206 and having a central opening 210 formed therein. A cylinder 212 having an inner diameter of about one inch is secured to the upper plate 208 at the central opening 210 and extends upward substantially perpendicular to the upper plate 208. The central opening 210 of the upper plate 208 should have a diameter at least equal to the inner diameter of the cylinder 212 where the cylinder 212 is mounted on top of the upper plate 208. However, the diameter of the central opening 210 may instead be sized large enough to receive the outer diameter of the cylinder 212 within the central opening 210 so that the cylinder 212 is secured to the upper plate 208 within the central opening 210.

Pin elements 214 are located near outside corners of the lower plate 206, and corresponding recesses 216 in the upper plate 208 are sized to receive the pin elements 214 to properly align and position the upper assembly 202 on the lower plate during testing. The weight of the upper assembly 202 (e.g., the upper plate 208 and cylinder 212) is suitable for simulating approximately 0.05 MPa, or about 3.45 dynes/square cm, pressure on the absorbent structure sample 218 during the FIFE Test.

To run the FIFE Test, the circular absorbent structure sample 218 having a diameter of approximately 3 in (approximately 7.6 cm) is weighed, with the tissue wrap on, and the weight is recorded in grams. The absorbent structure sample 218 is then centered on the lower plate 206 of the test apparatus 200 and the upper assembly 202 is placed over the absorbent structure sample 218 in opposed relationship with the lower plate 206, with the pin elements 214 of the lower plate 206 seated in the recesses 216 formed in the upper plate 208 and the cylinder 212 generally centered over the absorbent structure sample 218. A test solution (0.9 weight percent saline solution) is prepared with a small amount of blue dye added thereto. A first predetermined amount of the test solution (e.g., to simulate a first insult of the absorbent structure sample 218), corresponding to approximately 30 percent of the total retention capacity of the absorbent structure as determined by the Retention Capacity Test set forth above, is poured into a beaker. The test solution is then poured into the top of the cylinder 212 and allowed to flow down into the absorbent structure sample 218. A stopwatch is started when the first drop of solution contacts the absorbent structure sample 218 and is stopped when the liquid ring between the edge of the cylinder 212 and the absorbent structure sample 218 disappears. The reading on the stopwatch is recorded to two decimal places and represents the intake time (in seconds) required for the first insult to be taken into the absorbent structure sample 218.

A time period of fifteen minutes is allowed to elapse, after which a second insult equal to the first insult (e.g., to simulate a second insult of the absorbent structure to cumulatively achieve approximately 60 percent of the total retention capacity of the structure) is poured into the top of the cylinder 212 and again the intake time is measured as described above. After an additional fifteen minutes, the procedure is repeated for a third insult, also equal to the first insult, e.g., to simulate a third insult of the absorbent structure to cumulatively achieve approximately 90 percent of the total retention capacity of the absorbent structure sample 218.

An intake rate (e.g., in milliliters/second) for each of the three insults is determined by dividing the amount of liquid for each insult by the intake time measured for the corresponding insult.

While the FIFE Test as described above is typically conducted with the tissue wrap on the absorbent structure sample 218, in instances where the intake rate is expected to exceed about 6 ml/sec, the tissue wrap of the portion of the sample which faces the upper plate 208 of the test apparatus 200 should be removed and replaced with a flexible plastic screen having a mesh size of about 18 openings per inch to avoid impeding the flow of solution into the absorbent structure sample 218.

At least six samples of each absorbent structure are subjected to the FIFE Test and the results are averaged to determine the intake time and intake rate of the absorbent structure.

Cantilever Bending Test

Instructions:
1. Cut rectangular samples 1 inch wide and at least 6 inches long.
2. Place a piece of graph paper on a saline container.
3. Record the dimensions of the samples. Mark each sample top and bottom.
4. Weight each sample.
5. Measure the thickness (bulk) of each sample under a pressure of 0.05 psi.
6. Calculate sample density from thickness and weight.
7. Form a cantilever with the sample: place sample on some corner (of a block/table) and slowly increase the length of sample hanging in the cantilever fashion. Measure the extended length (L) and deflection distance (Y). The extended length must be at least 5 times longer than the deflection distance.
8. Turn sample over and repeat step 7 to measure the deflection on the other side.
9. A minimum of 6 replicates is advised and 10 is recommended.

Modulus calculation:

$$E = \frac{3}{2}\frac{\rho L^4}{z^2 Y}$$

ρ=density (lb/in³)
L=Length extended (inch)
Z=thickness (inch)
E=modulus (psi=lb/in²)
Y=deflection (inch)

Total Polysiloxane in Sheet

The polydimethyl siloxane content on the fluff pulp fiber materials, such as fluff pulp fibers, dry lap sheet comprising fluff pulp fibers, webs comprising fluff pulp fibers, and/or absorbent cores comprising fluff pulp fibers, was determined using the following procedure. A sample containing dimethyl siloxane is placed in a headspace vial, boron trifluoride reagent is added, and the vial sealed. After reacting for about fifteen minutes at about 100° C., the resulting Difluorodimethyl siloxane in the headspace of the vial is measured by gas chromatography using an FID detector.

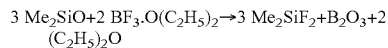
3 Me₂SiO+2 BF₃.O(C₂H₅)₂→3 Me₂SiF₂+B₂O₃+2 (C₂H₅)₂O

The method described herein was developed using a Hewlett-Packard Model 5890 Gas Chromatograph with an FID and a Hewlett-Packard 7964 autosampler. An equivalent gas chromatography system may be substituted.

The instrument was controlled by, and the data collected using, Perkin-Elmer Nelson Turbochrom software (version 4.1). An equivalent software program may be substituted. A J&W Scientific GSQ (30 m×0.53 mm i.d.) column with film thickness 0.25 μm, Cat. # 115-3432 was used. An equivalent column may be substituted.
Bath Temperature: 100° C.
Transfer Line Temperature: 120° C.
Vial Equilibrium Time: 15 minutes
Loop Fill Time: 0.2 minutes
Inject Time: 1.0 minute
Loop Temperature: 110° C.
GC Cycle Time: 25 minutes
Pressurize Time: 0.2 minutes
Loop Equil. Time: 0.05 minutes
Vial Shake: 1 (Low)

The Gas Chromatograph was set to the following instrument conditions:
Carrier gas: Helium
Flow rate: 16.0 mL through column and 14 mL make-up at the detector.
Injector Temperature: 150° C.
Detector Temperature: 220° C.

Chromatography Conditions:
50° C. for 4 minutes with a ramp of 10° C./minute to 150° C. Hold at final temperature for 5 minutes.
Retention Time: 7.0 min. for DFDMS A stock solution containing approximately 5000 μg/ml polydimethyl siloxane was prepared in the following manner. Approximately 1.25 grams of the polydimethyl siloxane emulsion is weighed to the nearest 0.1 mg into a 250-ml volumetric flask. The actual weight (represented as X) is recorded. Distilled water is added and the flask swirled to dissolve/disperse the emulsion. When dissolved/dispersed, the emulsion is diluted to volume with water and mixed. The ppm of the polysiloxane emulsion (represented as Y) is calculated from the following equation:

PPM polysiloxane emulsion $Y=X/0.250$

The Calibration Standards are made to bracket the target concentration by adding 0 (blank), 50, 100, 250, and 500 μL of the Stock Solution (the volume in uL $V_c$ recorded) to successive 20 mL headspace vials containing 0.1±0.001 grams of an untreated control fluff pulp fiber material. The solvent is evaporated by placing the headspace vials in an oven at a temperature ranging between about 60 to about 70° C. for 15 minutes. The μg of emulsion (represented as Z) for each calibration standard is calculated from the following equation:

$Z=Vc*Y/1000$

The calibration standards are then analyzed according to the following procedure: 0.100±0.001 g sample of a fluff pulp fiber material is weighed to the nearest 0.1 mg into a 20-ml headspace vial. The sample weight (represented as $W_s$) in mg is recorded. The amount of fluff pulp fiber material taken for the standards and samples must be the same.

100 μL of BF₃ reagent is added to each of the fluff pulp fiber material samples and calibration standards. Each vial is sealed immediately after adding the BF₃ reagent.

The sealed vials are placed in the headspace autosampler and analyzed using the conditions described previously, injecting 1 mL of the headspace gas from each fluff pulp fiber material sample and calibration standard.

A calibration curve of μg emulsion versus analyte peak area is prepared.

The analyte peak area of the fluff pulp fiber material sample is then compared to the calibration curve and amount of polydimethylsiloxane emulsion (represented as (A)) in μg on the fluff pulp fiber material determined.

The amount of polydimethylsiloxane emulsion (represented as (C)) in percent by weight on the fluff pulp fiber material sample is computed using the following equation:

$(C)=(A)/(W_s*10^4)$

The amount of the polydimethyl siloxane (represented as (D)) in percent by weight on the fluff pulp fiber material sample is computed using the following equation and the weight % polysiloxane (represented as (F)) in the emulsion:

$(D)=(C)*(F)/100$

Polydialkylsiloxane Content

The polydimethylsiloxane content on cellulose fluff pulp fiber substrates was determined using the following procedure. A sample containing polydimethylsiloxane is placed in a headspace vial, boron trifluoride reagent is added, and the vial sealed. After reacting for about fifteen minutes at about 100° C., the resulting Diflourodimethyl siloxane in the headspace of the vial is measured by gas chromatography with an FID detector.

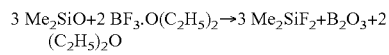
3 Me₂SiO+2 BF₃.O(C₂H₅)₂→3 Me₂SiF₂+B₂O₃+2 (C₂H₅)₂O

The method described herein was developed using a Hewlett-Packard Model 5890 Gas Chromatograph with an FID and a Hewlett-Packard 7964 autosampler. An equivalent gas chromatography system may be substituted.

The instrument was controlled by, and the data collected using, Perkin-Elmer Nelson Turbochrom software (version 4.1). An equivalent software program may be substituted. A J&W Scientific GSQ (30 m×0.53 mm i.d.) column with film thickness 0.25 μm, Cat. # 115-3432 was used. An equivalent column may be substituted.

The gas chromatograph was equipped with a Hewlett-Packard headspace autosampler, HP-7964 and set up at the following conditions:
Bath Temperature: 100° C.
Transfer Line Temperature: 120° C.
Vial Equilibrium Time: 15 minutes
Loop Fill Time: 0.2 minutes
Inject Time: 1.0 minute
Loop Temperature: 110° C.
GC Cycle Time: 25 minutes Pressurize Time: 0.2 minutes
Loop Equil. Time: 0.05 minutes
Vial Shake: 1 (Low)

The gas chromatograph was set to the following instrument conditions:
Carrier gas: Helium
Flow rate: 16.0 mL through column and 14 mL make-up at the detector.
Injector Temperature: 150° C.
Detector Temperature: 220° C.

Chromatography Conditions:
50° C. for 4 minutes with a ramp of 10° C./minute to 150° C. Hold at final temperature for 5 minutes.
Retention Time: 7.0 min. for DFDMS Preparation of Stock Solution The method is calibrated to pure PDMS using DC-200 fluid available from Dow Corning, Midland, Mich. A stock solution containing about 1250 µg/ml of the DC-200 fluid is prepared in the following manner. About 0.3125 grams of the DC-200 fluid is weighed to the nearest 0.1 mg into a 250-ml volumetric flask. The actual weight (represented as X) is recorded. A suitable solvent such as methanol, MIBK or chloroform is added and the flask swirled to dissolve/disperse the fluid. When dissolved the solution is diluted to volume with solvent and mixed. The ppm of dimethylpolysiloxane (represented as Y) is calculated from the following equation:

PPM of dimethylpolysiloxane $(Y)=X/0.250$

Preparation of Calibration Standards

The Calibration Standards are made to bracket the target concentration by adding 0 (blank), 50, 100, 250, and 500 µL of the Stock Solution (the volume in uL $V_c$ recorded) to successive 20 mL headspace vials containing 0.1±0.001 grams of an untreated control tissue web or tissue product. The solvent is evaporated by placing the headspace vials in an oven at a temperature ranging between about 60° C. to about 70° C. for about 15 minutes. The µg of dimethylpolysiloxane (represented as Z) for each calibration standard is calculated from the following equation:

$Z=Vc*Y/1000$

Analytical Procedure

The calibration standards are then analyzed according to the following procedure: 0.100±0.001 g of fluff pulp fiber material sample is weighed to the nearest 0.1 mg into a 20-ml headspace vial. The sample weight (represented as $W_s$) in mg is recorded. The amount of fluff pulp fiber material taken for the standards and samples must be the same.

100 µL of $BF_3$ reagent is added to each of the samples and calibration standards. Each vial is sealed immediately after adding the $BF_3$ reagent.

The sealed vials are placed in the headspace autosampler and analyzed using the conditions described previously, injecting 1 mL of the headspace gas from each fluff pulp fiber and standard.

Calculations

A calibration curve of µg dimethylpolysiloxane versus analyte peak area is prepared.

The analyte peak area of the fluff pulp fiber sample is then compared to the calibration curve and amount of polydimethylsiloxane (represented as (A)) in µg on the fluff pulp fiber, dry lap sheet, web, and/or absorbent core is determined.

The amount of polydimethylsiloxane (represented as (C)) in percent by weight on the tissue sample is computed using the following equation:

$(C)=(A)/(W_s*10^4)$

The amount of the polydimethylsiloxane (represented as (D)) in percent by weight on the tissue sample is computed using the following equation:

$(D)=(C)/100$

When polydialkylsiloxanes other than dimethylpolysiloxane are present, calibration standards are made from representative samples of the pure polydialkylsiloxanes that are present and the amount of each polydialkylsiloxane is determined as in the method above for polydimethylsiloxane. The sum of the individual polydialkylsiloxane amounts is then used for the total amount of polydialkylsiloxane present in the fluff pulp fiber material.

EXAMPLES

Example 1

Effect of Viscous Hydrophilic Polysiloxane on Fluff Pulp Fiber Absorbent Composite Properties: Liquid Handling and Rigidity Air-formed fluff pulp fiber absorbent composites were made with the different types of polysiloxane treated fluff pulp fibers at a basis weight of about 600 g/m² and a density of about 0.20 g/cm³.

A 785 g/m² Southern Softwood bleached kraft pulp fiber (commercially available from Weyerhaeuser located at Federal Way, Wash. under the trade designation of NB-416) processed into dry lap roll was cut into 8.5 inches by 11 inches sheets. Polysiloxane was coated on one side of the cut sheets of the dry lap roll at a target concentration of about 5 (wt) %+/−1% using a doctor blade. 5 cut sheets were treated for each code. The treated cut sheets of the dry lap roll were aged one week at ambient conditions. This aging step allowed the polysiloxane treatment composition to provide more homogeneous distribution, orientation, and interaction with cellulose fluff pulp fibers. The cut sheets of the dry lap roll were then fiberized using a fiberizer, commercially available from Kamas Industri AB located in Sweden. A series of hydrophobic polysiloxane and polysiloxane blend treatment compositions was investigated as set forth in Table I.

TABLE I

Description of polysiloxane treated fluff fibers.

| Fluff Code | Polysiloxane | Silicone/Chemical Supplier | Description | Viscosity (Cp) | Add-on (wt) % |
|---|---|---|---|---|---|
| Control | Control | | No treatment | — | — |
| C1 | DC-8600** | Dow Corning, Midland, MI | Blend amino-polysiloxane, fatty acid and polysiloxane polyether | 3000 | 5.3 |

TABLE I-continued

Description of polysiloxane treated fluff fibers.

| Fluff Code | Polysiloxane | Silicone/Chemical Supplier | Description | Viscosity (Cp) | Add-on (wt) % |
|---|---|---|---|---|---|
| Control | Control | | No treatment | — | — |
| C2 | Wacker Wetsoft CTW*** | Wacker, Duncan SC | Amino polyether polysiloxane | 2000-5000 | 5.2 |
| C3 | Wacker AF-23[4] | Wacker, Duncan SC | Diamino polysiloxane | 1000 | 5.4 |
| C4 | Wacker Wetsoft 648[5] | Wacker, Duncan SC | Polyether Polysiloxane (100% EO) | 40 | 5.3 |
| C5 | Wacker Wetsoft 9450[6] | Wacker, Duncan SC | Polyether Polysiloxane | 1000-3000 | 5.6 |
| C6 | Wacker AF-21[7] | Wacker, Duncan SC | Modified Amino (amido) polysiloxane | 2000 | 5.2 |
| C7 | Wacker M-642[8] | Wacker, Duncan SC | Carboxylic acid polysiloxane | 650 | 5.4 |
| C8 | Wacker Wetsoft AOP[9] | Wacker, Duncan SC | Modified Amino (amido) polysiloxane | 10 000 | 5.3 |
| C9 | 10% Wacker Wetsoft 648 90% AF-23 | Wacker, Duncan SC | Blend of amino polysiloxane with polysiloxane surfactant | >2000 assemble white | 4.9 |
| C10 | 30% Wacker Wetsoft 648 70% AF-23 | Wacker, Duncan SC | Blend of amino polysiloxane with polysiloxane surfactant | >2000 assemble white | 4.8 |
| A1 | DC-8175 | Dow Corning, Midland, MI | Amino silicone | 200 | 4.1 |
| A2 | DC-200-200Cp | Dow Corning, Midland, MI | Polydimethyl siloxane | 200 | 4.4 |
| B* | DC-200-5 Cp | Dow Corning, Midland, MI | Dow Corning, Midland, MI | 5 | 4.4 |
| A3 | Wacker IM-11[10] | Wacker, Duncan SC | Carbinol Polysiloxane (n = 11) | 50 | 4.4 |
| B1 | 1/3 DC-8600 2/3 DC-200 | Dow Corning, Midland, MI | Blend with amino and ether polysiloxanes | | 4.6 |
| B2 | 1/3 Wacker Wetsoft CTW 2/3 DC-200 | Wacker, Duncan SC | Blend with Amino polyether polysiloxane | | 4.5 |
| B4 | 1/3 Wacker Wetsoft 648 2/3 DC-200 | Wacker, Duncan SC | | | 4.2 |
| B8 | 10% Lecithin[11] 90% Mineral Oil[12] | | | ≈50 | 4.7 |

Chemical pre-treatment of the fluff pulp fibers with polysiloxane treatment composition drastically decreases the energy required for fiberization. The fiberization energy for the control, C6 and C1 fluff pulp fibers are 48.6 kW h/T, 31.1 kW h/T and 29.3 kW h/T, respectively. This represents about a 40% energy decrease with a 5% polysiloxane treatment composition add-on level.

The liquid handling properties and the rigidity of the fluff pulp fiber composites were measured. The Saturated Saline Capacity, Intake Rate Test ($1^{st}$ and $2^{nd}$ insults), density at testing and the Cantilever Bending Test are described above, and the results are reported in Table II. The average of 5 cut sheets for each code is reported.

TABLE II

Rigidity, Saline Capacity and Intake rates of Fluff Pulp Fiber Absorbent Composites.

| Code | Pulp Treatment/Pulp | Fluff Code | Initial density (g/cm3) | Young Modulus (psi) | Saturated Saline Capacity (g/g) | $1^{st}$ insult rate (mL/s) | $2^{nd}$ insult rate (mL/s) |
|---|---|---|---|---|---|---|---|
| 1 | NB-416 | Control | 0.12 | 85 | 6.72 | 3.52 | 1.94 |
| 2 | ND-416* | — | 0.13 | 200 | 6.26 | 4.59 | 2.93 |

TABLE II-continued

Rigidity, Saline Capacity and Intake rates of Fluff Pulp Fiber Absorbent Composites.

| Code | Pulp Treatment/ Pulp | Fluff Code | Initial density (g/cm3) | Young Modulus (psi) | Saturated Saline Capacity (g/g) | $1^{st}$ insult rate (mL/s) | $2^{nd}$ insult rate (mL/s) |
|---|---|---|---|---|---|---|---|
| 3 | CR 1654** | — | 0.15 | 215 | 6.97 | 2.84 | 1.18 |
| 4 | Wacker Wetsoft CTW | C2 | 0.14 | 1.9 | 4.9 | 1.81 | 0.6 |
| 5 | Wacker AF-23 | C3 | 0.14 | 1.2 | 0 | 0 | 0 |
| 6 | Wacker Wetsoft 648 | C4 | 0.14 | 4.6 | 3.73 | 2.12 | .75 |
| 7 | Wacker Wetsoft 9450 | C5 | 0.13 | 2.7 | 5.32 | 1.48 | .66 |
| 8 | Wacker M-642 | C7 | 0.14 | 0.9 | 5.53 | 0.19 | 0.4 |
| 9 | Wacker Wetsoft AOP | C8 | 0.14 | 0.7 | 6.31 | 0.11 | 0.35 |
| 10 | 90% mineral oil 10% lecithin | B8 | 0.12 | 1.3 | 6.86 | 1.90 | 0.89 |

*ND-416 is commercially available from Weyerhaeuser located at Federal Way, WA.
**CR 1654 is commercially available from Bowater located at Coosa Pines, AL.

The application of the polysiloxane treatment composition may affect the Fluff Pulp Fiber Absorbent Composite Saline Saturation Capacity. The fluff pulp fibers treated with highly substituted amino-functional polysiloxane treatment composition formed hydrophobic, non-wettable composites (Code 5); no liquid was absorbed. Polysiloxane treated (Code 9) and mineral oil treated (Code 10) fluff pulp fiber absorbent composites had specific saline capacities similar to untreated fluff pulp fibers absorbent composites (Codes 1-3). Polysiloxane chemistry may affect the specific saline capacity.

The absorbent composites made with polysiloxane treated fluff pulp fibers were significantly more flexible than the controlled made with commercial untreated (Code 1 and Code 3) or treated (Code 2). On average, fluff pulp fiber absorbent composites with the polysiloxane (5%) treated fluff pulp fibers were two orders of magnitude more flexible than those made with conventional non-treated fluff pulp fibers. Among the fluff pulp fiber composites made with polysiloxane treated fluff pulp fibers, flexibility increased from polyether polysiloxanes, amino glycol polysiloxane copolymer, and amino polysiloxanes.

The saline intake rates decrease from fluff pulp fiber composites made from conventional fibers (Codes 1-3), when compared to fluff pulp fiber absorbent composites including to polyether-functional polysiloxane treatment compositions, and amino-functional polysiloxane treatment compositions. The absorbent composites made with fluff pulp fibers treated with amino glycol-functional polysiloxane treatment compositions (Code 4) and polyether-functional polysiloxane treatment compositions (Codes 6 and 7) present advantageous balances of flexibility increase and liquid handling properties.

Example 2

Effect of Viscous Hydrophilic Polysiloxane on SAP/Fluff Pulp Fiber Absorbent Composite Properties: Compressibility Air-formed SAP/fluff pulp fiber absorbent composites were made with the different types of polysiloxane treated fluff pulp fibers described in Example 1 at a basis weight of about 600 g/m². The absorbent composites were compressed using a Press made by Carver, Inc. located at Wabash, Ind. at 18,000 psi for 30 seconds. The superabsorbent material used is commercially available under the trade designation of 9543 SXM from Stockhausen located at Greensboro, N.C. SAP/fluff pulp fiber absorbent composites were made at a mass ratio of 70:30.

The effect of polysiloxane treatment of the fluff pulp fibers on the ease of compressibility was measured by recording the effect of calendering on the SAP/fluff pulp fiber absorbent composite bulk achieved after each pass (see Table II). The target bulk was 1.5 mm and the nip pressure was constant at 3700 psi. A single steel-steel nip was used.

The target density was reached with only 1 pass through the calendar for the untreated fluff pulp fibers (Code 29), and the fluff pulp fibers treated with PDMS (Codes 22 and 28); 2 passes through the calendar were required with polysiloxanes functionalized with ether groups, carboxylic acid groups, carbinol and low concentration of amine (Codes 11-17, 19-20, and 25); 3 passes through the calendar were needed with codes with mineral oil/additive (Code 27), and some amino-functional polysiloxanes and their blends (Codes 18 and 24).

The SAP/fluff pulp fiber absorbent composites made with fluff pulp fibers treated with mineral oil/additive blends and blends of hydrophobic polysiloxane (high concentration of amine groups) are significantly more difficult to densify than fluff pulp fibers treated with more hydrophilic polysiloxanes: functionalized polysiloxanes with ether groups, carboxylic acid groups, carbinol, and low concentration of amine.

TABLE III

Debulker Setting for Polysiloxane Treated SAP/fluff Handsheets

| Code # | Code | 1st Pass Roll Gap Mm | 1st Pass Bulk Mm | 2nd Pass Roll Gap Mm | 2nd Pass Bulk mm | 3rd Pass Roll Gap Mm | 3rd Pass Bulk Mm |
|---|---|---|---|---|---|---|---|
| 11 | C1 | 1.25 | 2.1 | 0.56 | 1.45 | | |
| 12 | C2 | 1.25 | 2 | 0.63 | 1.42 | | |
| 13 | C3 | 1.25 | 2 | 0.63 | 1.45 | | |
| 14 | C4 | 1.25 | 1.6 | 0.89 | 1.41 | | |
| 15 | C5 | 1.25 | 1.8 | 0.89 | 1.44 | | |
| 16 | C6 | 1.25 | 2.1 | 0.63 | 1.47 | | |
| 17 | C7 | 1.25 | 1.9 | 0.63 | 1.4 | | |
| 18 | C8 | 1.25 | 2.1 | 0.63 | 1.68 | 0.63 | 1.45 |
| 19 | C9 | 1.25 | 2 | 0.63 | 1.45 | | |
| 20 | C10 | 1.25 | 2.1 | 0.63 | 1.48 | | |
| 21 | A1 | no sample | | | | | |
| 22 | A2 | 1.25 | 1.45 | | | | |
| 23 | A3 | no sample | | | | | |
| 24 | B1 | 1.25 | 2.2 | 0.63 | 1.66 | 0.63 | 1.44 |
| 25 | B2 | 1.25 | 2 | 0.63 | 1.51 | | |
| 26 | B4 | no sample | | | | | |
| 27 | B8 | 1.25 | 2.1 | 0.63 | 1.8 | 0.56 | 1.48 |
| 28 | B* | 1.25 | 1.45 | | | | |
| 29 | NB-416 | 1.25 | 1.4 | | | | |

Nip pressure 3700 psi
Target bulk 1.5 mm

Example 3

Effect of Polysiloxane Chemistry (Viscous Hydrophilic) on SAP/Fluff Pulp Fiber Absorbent Composite Properties The effect of polysiloxane chemistry on the properties of high SAP content and thin absorbent composites was investigated. Fluff pulp fibers were treated with a series of viscous hydrophilic polysiloxane treatment compositions applied at about 5 (wt) % on fluff pulp fibers and absorbent composites were made using a conventional SAP.

Air-formed SAP/fluff pulp fiber absorbent composites were made with the different types of polysiloxane treated fluff pulp fibers described in Example 1 at a basis weight of about 600 g/m² and a density of about 0.4 g/cm³. Superabsorbent material, commercially available under the trade designation of 9543 SXM from Stockhausen located at Greensboro, N.C. SAP/fluff pulp fiber absorbent composites were made at a mass ratio of 70:30.

The liquid handling properties and the rigidity of the fluff pulp fiber absorbent composites were measured. The Saturated Saline Capacity, Intake Rate Test ($1^{st}$ and $2^{nd}$ insults), density at testing and the Cantilever Bending Test are described above, and the results are reported in Table IV. The average of 5 cut sheets for each code is reported.

TABLE IV

Rigidity, Saline Capacity and Intake rates of SAP/Fluff Pulp Fiber Absorbent Composites.

| Code | Pulp Treatment/ Pulp | Fluff Code | Initial Density (g/cm3) | Young Modulus (psi) | Saturated Saline Capacity (g/g) | $1^{st}$ insult rate (mL/s) | $2^{nd}$ insult rate (mL/s) |
|---|---|---|---|---|---|---|---|
| 30 | NB-416 | Control | 0.41 | 2165 | 18.2 | 0.97 | 1.11 |
| 31 | ND-416 | — | 0.36 | 983 | 18.7 | 1.02 | 1.74 |
| 32 | CR 1654 | — | 0.37 | 1208 | 18.2 | 0.91 | 1.24 |
| 33 | DC-8600 | C1 | 0.28 | 4 | 16.3 | 0.21 | 0.14 |
| 34 | Wacker Wetsoft CTW | C2 | 0.33 | 7 | 17.0 | 0.38 | 0.21 |
| 35 | Wacker AF-23 | C3 | 0.38 | 7 | 11.9 | 0.04 | 0.06 |
| 36 | Wacker Wetsoft 648 | C4 | 0.39 | 35 | 17.8 | 0.53 | 0.11 |
| 37 | Wacker Wetsoft 9450 | C5 | 0.37 | 15 | 18.0 | 0.45 | 0.36 |
| 38 | Wacker M-642 | C7 | 0.39 | 18 | 17.7 | 0.31 | 0.35 |
| 39 | Wacker Wetsoft AOP | C8 | 0.35 | 4 | 16.2 | 0.23 | 0.20 |
| 40 | 10% Wacker Wetsoft 648 90% AF-23 | C9 | 0.35 | 24 | 17.8 | 0.35 | 0.44 |
| 41 | 30% W 648 70% AF-23 | C10 | 0.33 | 13 | 18.0 | 0.51 | 0.22 |
| 42 | 90% mineral oil 10% lecithin | B8 | 0.33 | 4 | 17.9 | 0.39 | 0.22 |

Fluff pulp fiber treatment with polysiloxane treatment compositions, prior to forming into absorbent composites, is very efficient in decreasing the rigidity of SAP/fluff pulp fiber absorbent composites. Structure rigidity, measured with the Young Modulus (E), decreases by almost three orders of magnitude with the polysiloxane treated fluff pulp fibers. The absorbent composites made with commercially available non-treated fluff pulp fibers had a rigidity higher than about 1000 psi (Codes 30-32); rigidity of the fluff pulp fiber absorbent composites made with the polysiloxane treated fluff pulp fibers ranged from about 35 psi (Code 36) to about 4 psi (Codes 33, 39, and 42). Treatment with amino-functional polysiloxane treatment compositions (Codes 35 and 39) tended to decrease the structure rigidity of fluff pulp fiber composite slightly more than polyether-functional polysiloxane treatment compositions (Code 36 and 37). In between are the blends amino/polyether-functional polysiloxane treatment compositions (Code 33, 40, and 41) and the amino glycol-functional polysiloxane copolymer treatment compositions (Code 34).

Specific Saturated Saline capacity of absorbent composites was little affected by the application of the polysiloxane treatment compositions. Fluff pulp fibers treated with the most hydrophobic polysiloxane treatment compositions (amino-functional polysiloxanes and blends, such as Codes 55 and 53) produced fluff pulp fiber absorbent composites with a lower capacity that those made with non-treated fluff pulp fibers (Codes 50-52).

Liquid intake of the absorbent composites is affected by the application of polysiloxane treatment compositions and polysiloxane treatment composition chemistries. While all polysiloxane treated fluff pulp fiber absorbent composites had a lower first and second insult rate that those made with non-treated fluff pulp fibers (Code 30-32), the intake rate of the fluff pulp fiber absorbent composites with fluff pulp fibers treated with hydrophilic polysiloxane treatment compositions such as polyether functional polysiloxanes (Codes 36 and 37), amino glycol-functional polysiloxanes (Code 34), carboxylic acid-functional polysiloxanes (Code 58) and blends with those polysiloxanes (Codes 40 and 41) was significantly better than absorbent composites made with fluff pulp fibers treated with hydrophobic polysiloxanes such as amino-functional polysiloxanes (Code 35).

Overall, fluff pulp fiber absorbent composites made with fluff pulp fibers treated with hydrophilic polysiloxanes had better properties than the control.

Example 4

Effect of Polysiloxane Concentration on Fluff Pulp Fiber/SAP Absorbent Composite Properties The effect of polysiloxane concentration on the properties of high SAP content thin absorbent composites was investigated. The fluff pulp fibers were treated with different concentration of hydrophilic polysiloxanes, and absorbent composites were made using a conventional SAP. The polysiloxane concentration on fluff pulp fibers was varied by applying different amounts of polysiloxane to fluff pulp fiber sheets as described in Example 1.

Air-formed SAP/fluff pulp fiber absorbent composites were made at a basis weight of about 600 g/m² and a density of about 0.38 g/cm³+/−0.05 g/cm³. Stockhausen 9543 SXM, a high stiffness, mid liquid SAP was selected. SAM/fluff composites were made at a mass ratio of 70:30.

The liquid handling properties and the rigidity of the fluff pulp fiber absorbent composite were measured. The Intake Rate Test and the Cantilever Bending Test are described above, and the results are reported in Table V. The average of 5 cut sheets for each code is reported Increasing polysiloxane concentration on the polysiloxane treated fluff pulp fibers decreased the rigidity and liquid intake rate of the absorbent composites comprising the polysiloxane treated fluff pulp fibers. A better balance of properties was achieved with the absorbent composites comprising the polysiloxane treated fluff pulp fibers treated with lower concentrations of hydrophilic polysiloxane treatment compositions such as amino glycol-functional polysiloxane copolymers and polyether-functional polysiloxanes (Codes 45-47).

TABLE V

Rigidity, Saline Capacity and Intake rates of SAP/Fluff Pulp Fiber Absorbent Composites.

| Code | Pulp Treatment polysiloxane type and concentration | Initial density (g/cm3) | Young Modulus (psi) | Saturated Saline Capacity (g/g) | 1st insult rate (mL/s) | 2nd insult rate (mL/s) |
|---|---|---|---|---|---|---|
| 43 | NB 416 | 0.37 | 1436 | 19.2 | 0.94 | 1.60 |
| 44 | W 648%-2% | 0.43 | 931 | 18.6 | 0.54 | 0.24 |
| 45 | W 9450-2% | 0.40 | 137 | 17.9 | 0.48 | 0.34 |
| 46 | W CTW-1% | 0.35 | 19 | 18.1 | 0.48 | 0.35 |
| 47 | W CWT-2% | 0.34 | 11 | 18.0 | 0.47 | 0.40 |
| 48 | W CWT-4% | 0.38 | 17 | 18.2 | 0.43 | 0.34 |
| 49 | AF23-1% | 0.35 | 10 | 17.4 | 0.20 | 0.25 |
| 50 | AF 23-2% | 0.35 | 10 | 16.8 | 0.16 | 0.18 |
| 51 | AF 23-4% | 0.36 | 9 | 16.7 | 0.07 | 0.09 |

Example 5

Effect of Polysiloxane Concentration and Chemistry on Fluff Pulp Fiber/SAP Absorbent Composite Properties The effect of polysiloxane concentration on the properties of high SAP content thin absorbent composites was investigated. Fluff pulp fibers were treated with 2 different concentrations of hydrophilic polysiloxanes. The absorbent composites were made using a high performance SAP. Two types of polysiloxane treatment compositions are compared. Polysiloxane concentration on the polysiloxane treated fluff pulp fibers was varied by applying different amounts of polysiloxane treatment composition to the cut sheets of the dry lap roll and by blending the polysiloxane treated fluff pulp fibers with nontreated fluff pulp fibers.

Polysiloxane was applied on both sides of a 785 g/m² Southern Softwood bleached kraft fluff pulp fiber (commercially available from Weyerhaeuser located at Federal Way, Wash. under the trade designation of NB-416,) processed into a dry lap roll, using a uniform fluid dispenser (UFD). The converting line consisted of an unwinder, a UFD applicator (Dynatech) and a winder operated in series. Polysiloxane treatment composition was applied at a target concentration of 1.5 (wt) % or 0.75 wt (%), with half on each side. The fluff pulp fiber was aged a minimum of 1 week prior to use. Two polysiloxane treatment composition chemistries were investigated: Wetsoft CTW and Wetsoft 9450, both from Wacker Chemical located at Duncan, S.C.

Air-formed SAP/fluff pulp fiber absorbent composites were made at a basis weight of approximately 566 g/m² and a density of about 0.37 g/cm³. Blending of the polysiloxane treated pulp was made with fluff pulp fiber commercially available from Weyerhaeuser located at Federal Way, WA under the trade designation of CF-416, and ND-416.The SAP:fluff pulp fiber mass ratio was 70:30. A high performance SAP available from BASF located in Ludwigshafen, Germany under the trade designation Multicomponent Superabsorbent Particulate gel (MSP) was selected. One such material, BASF E1231-99, has a fecal fluid AUL of 0.3 psi at 27.1 grams/gram and a saline AUL at 0.3 psi of 33.0 grams/gram. Multicomponent superabsorbent gel particles and methods to prepare them are described in U.S. Pat. No. 5,981,689 issued to Mitchell et al. on Nov. 9, 1999; U.S. Pat. No. 6,072,101 issued to Beihoffer on Jun. 6, 2000; U.S. Pat. No. 6,087,448 issued to Mitchell et al. on Jul. 11, 2000; U.S. Pat. No. 6,121,409 issued to Mitchell et al. on Sep. 19, 2000; U.S. Pat. No. 6,159,591 issued to Beihoffer et al. on Dec. 12, 2000; U.S. Pat. No. 6,194,631 issued to Mitchell et al. on Feb. 27, 2001; U.S. Pat. No. 6,222,091 issued to Beihoffer et al. on Apr. 24, 2001; U.S. Pat. No. 6,235,965 issued to Beihoffer et al. on May 22, 2001; U.S. Pat. No. 6,342,298 issued to Evans et al. on Jan. 29, 2002; U.S. Pat. No. 6,376,072 issued to Evans et al. on Apr. 23, 2002; U.S. Pat. No. 6,392,116 issued to Beihoffer et al. on May 21, 2002; U.S. Pat. No. 6,509,512 issued to Beihoffer et al. on Jan. 21, 2003; and, U.S. Pat. No. 6,555,502 issued to Beihoffer et al. on Apr. 29, 2003; U.S. Patent Publication No. 2001/01312; U.S. Patent Publication No. 2001/07064; U.S. Patent Publication No. 2001/29358; U.S. Patent Publication No. 2001/44612; U.S. Patent Publication No. 2002/07166; U.S. Patent Publication No. 2002/15846; and, U.S. Patent Publication No. 2003/14027; and, PCT Publication No. WO 99/25393; PCT Publication No. WO 99/25745; PCT Publication No. WO 99/25748; PCT Publication No. WO 00/56959; PCT Publication No. WO 00/63295; PCT Publication No. WO 02/10032; PCT Publication No. WO 03/18671; and, PCT Publication No. WO 03/37392; the disclosures of which are incorporated herein by reference to the extent that they are non-contradictory herewith.

Liquid handling and mechanical properties were performed as described. The averages of 5 cut sheets for each code are described in Table VI.

vide the absorbent composite with a marked flexibility increase with a moderate absorbency impact.

The absorbent composites comprising polysiloxane treated fluff pulp fibers treated with the amino glycol-functional polysiloxane (Wetsoft CTW) are more flexible than polysiloxane treated fluff pulp fibers treated with the polyether polysiloxane (Wetsoft 9450), at a same polysiloxane dosage of 1.5% and less (1.5%: code 53 versus 58, 0.75% code 56 versus 59).

Using a high performance SAP did not increase the specific Saturated Capacities nor the rigidity of the fluff pulp fiber absorbent composite (Code 61 versus Code 43). However, the intake rates of the absorbent compositions for all insults increased.

Example 6

Effect of Blending Polysiloxane Treated Fibers on Fluff Pulp Fiber/SAP Absorbent Composite Properties The effect of polysiloxane concentration on the properties of high SAP content thin fluff pulp fiber absorbent composite was investigated. Fluff pulp fibers were treated with 2 different concentrations of an amino glycol-functional polysiloxane copolymer treatment compositions, and absorbent composites were made using a regular SAP. The polysiloxane concentration on fluff pulp fibers was varied by applying different amounts of polysiloxane to pulp sheets, as described in Example 5, and by blending those polysiloxane treated fluff pulp fibers with non-treated fluff pulp fibers.

TABLE VI

Rigidity, Saline Capacity and Intake rates of SAP/Fluff Pulp Fiber Absorbent Composites.

| Code | Pulp Treatment polysiloxane type and concentration | Polysiloxane concentration on fibers | Initial density (g/cm3) | Young Modulus (psi) | Saturated Saline Capacity (g/g) | $1^{st}$ insult rate (mL/s) | $2^{nd}$ insult rate (mL/s) |
|---|---|---|---|---|---|---|---|
| 53 | W CTW (1.5%) | 1.5% | 0.29 | 18 | 17.9 | 0.72 | 2.17 |
| 54 | W CTW (1.5%)/CF | 0.75% | 0.28 | 97 | 17.8 | 0.78 | 2.16 |
| 55 | W CTW (1.5%)/ND | 0.75% | 0.30 | 191 | 18.8 | 0.75 | 2.37 |
| 56 | W CTW (0.75%) | 0.75% | 0.31 | 217 | 18.8 | 0.73 | 2.05 |
| 57 | WCTW (0.75%)/CF | 0.38% | 0.30 | 154 | 17.9 | 0.77 | 2.13 |
| 58 | W 9450 (1.5%) | 1.5% | 0.31 | 117 | 17.9 | 0.74 | 2.27 |
| 59 | W 9450 (0.75%) | 0.75% | 0.32 | 218 | 17.3 | 0.78 | 2.23 |
| 60 | W9450 (0.75%)/CF | 0.38% | 0.25 | 213 | 18.3 | 0.77 | 1.78 |
| 61 | CF 416 | — | 0.33 | 1572 | 18.9 | 1.13 | 4.06 |
| 62 | ND 416 | — | 0.36 | 987 | 18.6 | 1.11 | 3.64 |
| 63 | ND/CF | — | 0.33 | 1413 | 18.3 | 1.06 | 3.37 |

The rigidity of the absorbent composite increases as the polysiloxane treatment composition concentration on the polysiloxane treated fluff pulp fiber decreases. The absorbent composites were made with polysiloxane fluff pulp fibers containing respectively 1.5% (wt), 0.75% (wt), and 0.38% (wt) polysiloxane were more flexible by a factor of 87 (Code 53), 16 (Code 58), and 10 (Code 57) than the control made with nontreated fluff pulp fibers (Code 61). For these same absorbent composites, the first insult rates were lower by only 36% for those made with polysiloxane treated fluff pulp fibers treated with 1.5% polysiloxane treatment composition (Code 53), 35% for 0.75% (Code 58), and 32% for 0.38% (Code 57) compare to the control (Code 61). The respective second insult rates were lower by only 47%, 44%, and 48%. It can be seen that polysiloxane treatment of the fluff pulp fibers pro- Two polysiloxane treatment composition chemistries were investigated: Wetsoft CTW and Wetsoft 9450, both available from Wacker Chemical located at Duncan, S.C.

Air-formed SAP/fluff pulp fiber absorbent composites were made at a basis weight of about 600 g/m$^2$ and a density of about 0.32 g/cm$^3$ +/−0.06 g/cm$^3$. Stockhausen 9543 SXM, a high stiffness, mid liquid capacity SAP was selected. The absorbent composites were made at a SAP/fluff pulp fiber mass ratio of 70:30.

The liquid handling properties and the rigidity of the fluff pulp fiber absorbent composites were measured. The Intake Rate Test and the Cantilever Bending Test are described above, and the results are reported in Table VII. The average of 5 cut sheets of each code is reported.

TABLE VII

Rigidity, Saline Capacity and Intake rates of SAP/Fluff Pulp Fiber Absorbent Composites.

| Code | Pulp Treatment polysiloxane type and concentration | Polysiloxane CTW | Initial density (g/cm3) | Young Modulus (psi) | Saturated Saline Capacity (g/g) | 1st insult rate (mL/s) | 2nd insult rate (mL/s) |
|---|---|---|---|---|---|---|---|
| 64 | NB 416 | — | 0.37 | 1846 | 18.9 | 0.76 | 1.06 |
| 65 | 25:75 (1.5% CTW/NB) | 0.38% | 0.32 | 239 | 18.6 | 0.56 | 0.57 |
| 66 | 50:50 (0.75% CTW/NB) | 0.38% | 0.30 | 48 | 19.1 | 0.59 | 0.64 |
| 67 | 50:50 (1.5% CTW/NB) | 0.75% | 0.32 | 33 | 18.6 | 0.53 | 0.48 |
| 68 | 75:25 (1.5% CTW/NB) | 1.13% | 0.32 | 9 | 18.8 | 0.49 | 0.48 |
| 69 | 100% (0.75% CTW) | 0.75% | 0.28 | 3 | 18.1 | 0.48 | 0.45 |
| 70 | 100% (1.5% CTW) | 1.5% | 0.31 | 6 | 18.2 | 0.38 | 0.27 |

The fluff pulp fiber absorbent composites specific saline capacities are independent from the polysiloxane treatment composition chemistry and the concentration applied (for these low polysiloxane concentrations). The rigidity of the fluff pulp fiber absorbent composites decrease as the concentration of polysiloxane on the fluff pulp fibers (Codes 64, 69, and 70) increases.

At a same polysiloxane concentration on fluff pulp fibers (at low polysiloxane concentration), a lower rigidity for the fluff pulp fiber absorbent composite is achieved by applying a lower polysiloxane concentration to as many fluff pulp fibers as possible in a dry lap roll, rather than blending polysiloxane treated fluff pulp fibers with a higher polysiloxane dosage with nontreated fluff pulp fibers (0.75%: Code 69 versus Code 67, 0.38%: Code 65 versus Code 66); $1^{st}$ and $2^{nd}$ insult rates are basically unaffected by the blending of polysiloxane treated fluff pulp fibers and nontreated fluff pulp fibers.

Treating fluff pulp fiber dry lap with low concentrations of hydrophilic polysiloxane prior to fiberization and air-formation of SAP/fluff pulp fiber absorbent composites, provides a significant decrease in the structure rigidity and an increase in its conformability with minimal impact on liquid intake.

While the absorbent composites of the present invention have been described in detail with respect to specific aspects thereof, it will be appreciated that those skilled in the art, upon attaining an understanding of the foregoing, may readily conceive of alterations to, variations of and equivalents to these absorbent composites. Accordingly, the scope of the present invention should be assessed as that of the appended claims and any equivalents thereto.

We claim:

1. An absorbent core comprising fluff pulp fiber treated with polysiloxane, wherein the absorbent core has a density of about 0.15 g/cm$^3$ or greater and a Young's modulus of about 75 psi or less, and wherein the polysiloxane has a general structure of:

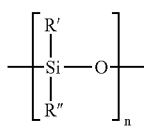

wherein:

n is an integer $\geq 2$;

each R' and R" moiety comprises independently an organofunctional group and non-organofunctional group or mixtures thereof.

2. The absorbent core of claim 1, wherein the absorbent core has a first insult rate of about 1 mL/s or greater.

3. The absorbent core of claim 1, wherein the absorbent core has a basis weight of about 150 g/m$^2$ or greater.

4. The absorbent core of claim 1, wherein the polysiloxane comprises an amino-functional moiety.

5. The absorbent core of claim 1, wherein the amino-functional moiety is selected from the group of primary amine, secondary amine, tertiary amine, quaternary amine, unsubstituted amide, and mixtures thereof.

6. The absorbent core of claim 1, wherein the fluff pulp fibers are treated with the polysiloxane before the absorbent core is formed.

7. The absorbent core of claim 1, further comprising superabsorbent material.

8. The absorbent core of claim 2, further comprising superabsorbent material.

9. A disposable absorbent product containing the absorbent core of claim 1 or claim 7.

10. A disposable absorbent product containing the absorbent core of claim 2 or claim 8.

11. An absorbent core comprising
   a) fluff pulp fiber treated with polysiloxane; and,
   b) superabsorbent material;

wherein the absorbent core has a superabsorbent content of about 25% or greater, a density of about 0.25 g/$^3$ or greater, and a Young's modulus of about 500 psi or less, and wherein the polysiloxane has a general structure of:

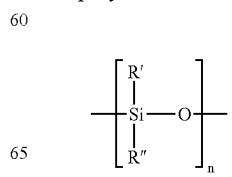

wherein:

n is an integer $\geq 2$;

each R' and R" moiety comprises independently an organofunctional group and non-organofunctional group or mixtures thereof.

12. The absorbent core of claim 11, wherein the absorbent core has a first insult rate of about 0.7 mL/s or greater and a second insult rate of about 2 mL/s or greater.

13. The absorbent core of claim 11, wherein the absorbent core has a basis weight of about 50 g/m² or greater.

14. The absorbent core of claim 11, wherein the polysiloxane comprises an amino-functional moiety.

15. The absorbent core of claim 11, wherein the amino-functional moiety is selected from the group of primary amine, secondary amine, tertiary amine, quaternary amine, unsubstituted amide, and mixtures thereof.

16. The absorbent core of claim 11, wherein the fluff pulp fibers are treated with the polysiloxane before the absorbent core is formed.

17. A disposable absorbent product containing the absorbent core of claim 11.

18. A disposable absorbent product containing the absorbent core of claim 12.

19. An absorbent core comprising a) fluff pulp fiber treated with polysiloxane; and, b) superabsorbent material;

wherein the absorbent core has a superabsorbent content of about 25% or greater, has a density of about 0.25 g/cm³ or greater, and a Young's modulus of about 500 psi or less and wherein the polysiloxane has a general structure of:

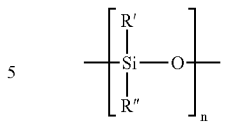

wherein:

n is an integer $\geq 2$;

each R' and R" moiety comprises independently an organofunctional group and non-organofunctional group or mixtures thereof.

20. The absorbent core of claim 19, wherein the absorbent core has a first insult rate of about 0.7 mL/s or greater and a second insult rate of about 2 mL/s or greater.

21. The absorbent core of claim 19, wherein the absorbent core has a basis weight of about 50 g/m² or greater.

22. The absorbent core of claim 19, wherein the polysiloxane comprises an amino-functional moiety.

23. The absorbent core of claim 19, wherein the amino-functional moiety is selected from the group of primary amine, secondary amine, tertiary amine, quaternary amine, unsubstituted amide, and mixtures thereof.

24. The absorbent core of claim 19, wherein the fluff pulp fibers are treated with the polysiloxane before the absorbent core is formed.

25. A disposable absorbent product containing the absorbent core of claim 19.

26. A disposable absorbent product containing the absorbent core of claim 20.

* * * * *